US008858587B2

(12) United States Patent
Ierulli

(10) Patent No.: US 8,858,587 B2
(45) Date of Patent: Oct. 14, 2014

(54) NASAL DILATOR AND METHOD OF MANUFACTURE

(75) Inventor: Joseph Vincent Ierulli, Portland, OR (US)

(73) Assignee: Corbett Lair, Inc., Vancouver, WA (US)

(*) Notice: Subject to any disclaimer, the term of this patent is extended or adjusted under 35 U.S.C. 154(b) by 578 days.

(21) Appl. No.: 12/402,214

(22) Filed: Mar. 11, 2009

(65) Prior Publication Data

US 2009/0234383 A1 Sep. 17, 2009

Related U.S. Application Data

(60) Provisional application No. 61/035,972, filed on Mar. 12, 2008.

(51) Int. Cl.
*A61M 29/00* (2006.01)
*A61F 5/08* (2006.01)

(52) U.S. Cl.
CPC ........................... *A61F 5/08* (2013.01)
USPC ........... 606/199; 156/252; 156/253; 156/268; 128/207.18

(58) Field of Classification Search
USPC ............. 606/199, 196, 204.25; 156/250, 256, 156/263, 264, 265, 271, 269, 252, 253, 156/268; 128/200.24, 207.18, 848
See application file for complete search history.

(56) References Cited

U.S. PATENT DOCUMENTS

| | | | |
|---|---|---|---|
| 5,476,091 A | 12/1995 | Johnson | |
| 5,479,944 A | 1/1996 | Petruson | |
| 5,533,499 A | 7/1996 | Johnson | |
| 5,533,503 A | 7/1996 | Doubek et al. | |
| 5,546,929 A | 8/1996 | Muchin | |
| 5,549,103 A | 8/1996 | Johnson | |
| RE35,408 E | 12/1996 | Petruson | |
| 5,611,333 A | 3/1997 | Johnson | |
| 5,653,224 A | 8/1997 | Johnson | |
| 5,695,846 A * | 12/1997 | Lange et al. | 428/98 |
| 5,706,800 A | 1/1998 | Cronk et al. | |
| 5,718,224 A * | 2/1998 | Muchin | 128/200.24 |
| 5,769,089 A | 6/1998 | Hand et al. | |
| 5,820,578 A * | 10/1998 | Johansen | 602/57 |
| 5,890,486 A * | 4/1999 | Mitra et al. | 128/200.24 |
| 5,931,854 A | 8/1999 | Dillon | |
| 5,957,126 A | 9/1999 | Neeser | |
| 5,985,081 A * | 11/1999 | Reynolds | 156/271 |
| 6,006,746 A | 12/1999 | Karell | |
| 6,029,658 A | 2/2000 | De Voss | |
| 6,058,931 A | 5/2000 | Muchin | |
| 6,065,470 A | 5/2000 | Van Cromvoirt et al. | |
| 6,098,616 A * | 8/2000 | Lundy et al. | 128/200.24 |

(Continued)

FOREIGN PATENT DOCUMENTS

ES 289-561 10/1985

*Primary Examiner* — Darwin Erezo
*Assistant Examiner* — Katrina Stransky
(74) *Attorney, Agent, or Firm* — Mersenne Law LLP

(57) ABSTRACT

A nasal dilator manufacturing process reduces waste by cutting nested strips of flexible resilient members interconnected by waste webs from a sheet of resilient-layer material. The nested strips are incorporated into a fabrication matrix with other layers (e.g. base or cover layers), then individual nasal dilators are formed by cutting through the matrix around a peripheral outline of a dilator, said cutting severing the nested strips that are part of the fabrication matrix near the waste webs between the flexible resilient members.

26 Claims, 14 Drawing Sheets

(56) References Cited

U.S. PATENT DOCUMENTS

| | | |
|---|---|---|
| 6,196,228 B1 | 3/2001 | Kreitzer et al. |
| 6,244,265 B1 | 6/2001 | Cronk et al. |
| 6,276,360 B1 | 8/2001 | Cronk et al. |
| 6,318,362 B1 | 11/2001 | Johnson |
| 6,357,436 B1 | 3/2002 | Kreitzer et al. |
| 6,375,667 B1 | 4/2002 | Ruch |
| 6,453,901 B1 * | 9/2002 | Ierulli ............ 128/200.24 |
| 6,550,474 B1 | 4/2003 | Anderson et al. |
| 6,656,311 B2 * | 12/2003 | Venturino et al. ....... 156/259 |
| 6,694,970 B2 | 2/2004 | Spinelli et al. |
| 6,702,917 B1 * | 3/2004 | Venturino et al. ....... 156/252 |
| 6,769,428 B2 | 8/2004 | Cronk et al. |
| 6,769,429 B1 | 8/2004 | Benetti |
| 6,780,272 B2 * | 8/2004 | Wood ............ 156/250 |
| 7,067,710 B1 | 6/2006 | Beaudry |
| 7,114,495 B2 | 10/2006 | Lockwood, Jr. |
| 7,541,510 B2 * | 6/2009 | Beaudry ............ 602/41 |
| 8,062,329 B2 | 11/2011 | Ierulli |
| 2002/0000227 A1 * | 1/2002 | Duyke et al. ......... 128/200.24 |
| 2006/0233995 A1 * | 10/2006 | Garland ............ 428/41.8 |
| 2006/0246248 A1 * | 11/2006 | Van Dyke ............ 428/43 |
| 2008/0257341 A1 | 10/2008 | Ierulli |
| 2009/0234383 A1 | 9/2009 | Ierulli |
| 2011/0093004 A1 | 4/2011 | Ierulli |
| 2011/0295312 A1 | 12/2011 | Ierulli |

* cited by examiner

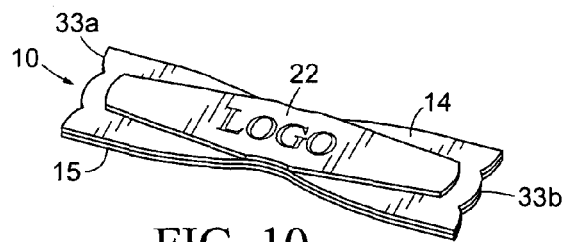
FIG. 10
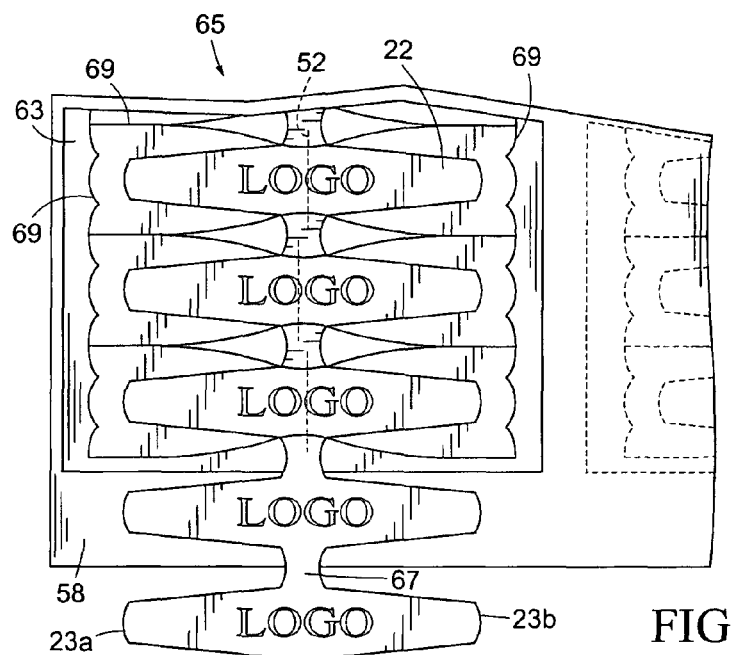
FIG. 11
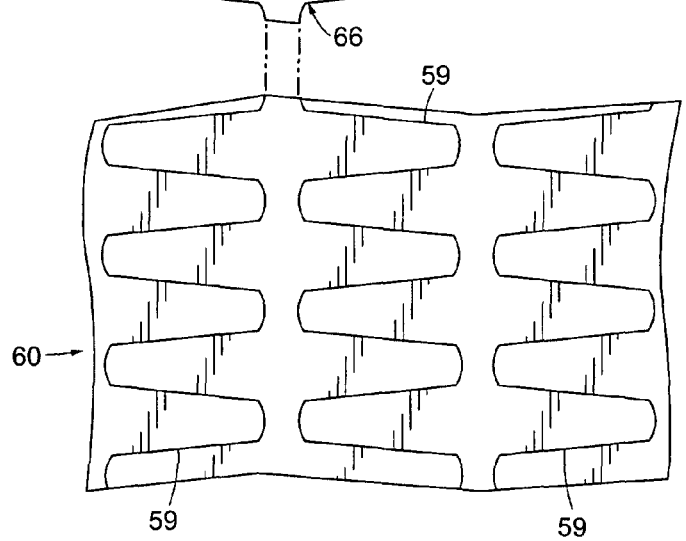

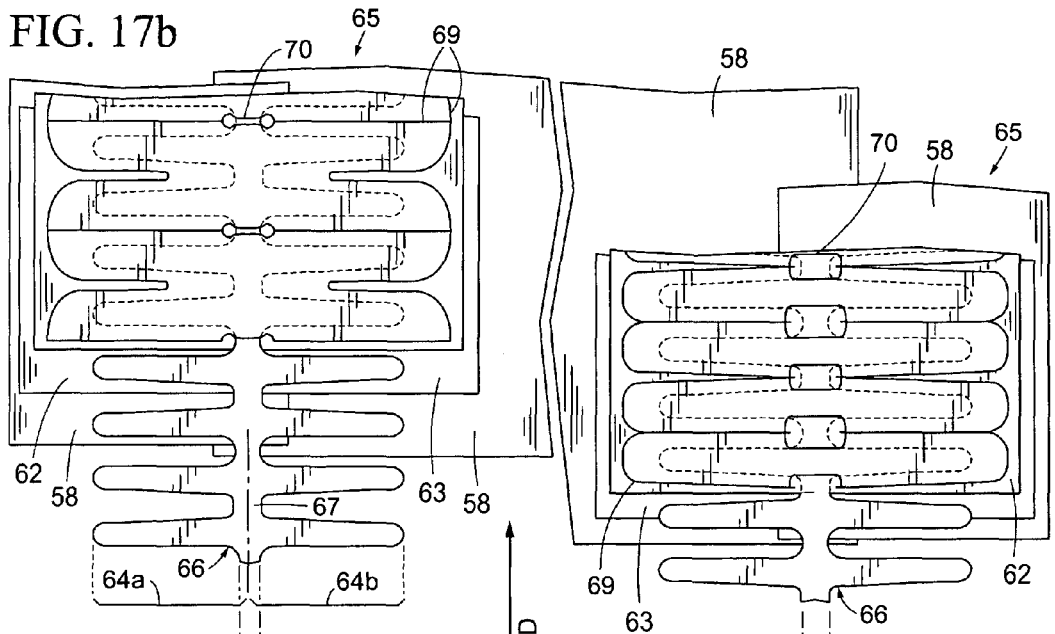
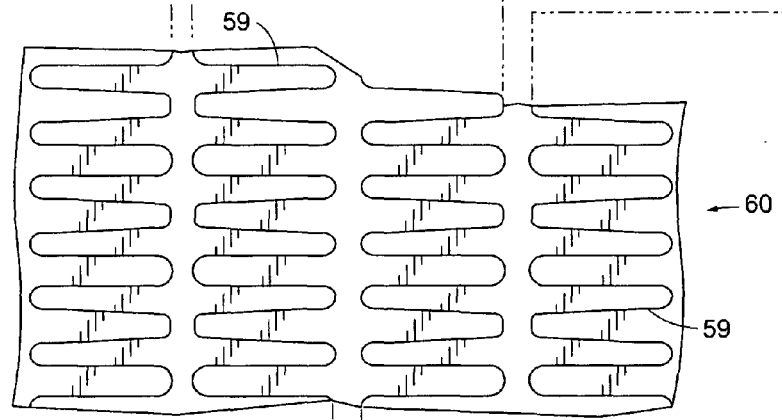
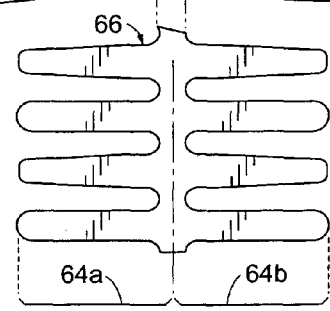
FIG. 17b
FIG. 17c
FIG. 17a

NASAL DILATOR AND METHOD OF MANUFACTURE

RELATED APPLICATIONS

This application claims the benefit of U.S. Provisional Application No. 60/888,543 filed Feb. 6, 2007 and 61/035,972 filed Mar. 12, 2008.

FIELD OF THE INVENTION

The present invention relates to apparatus and methods of dilating external tissue. As disclosed and taught in the preferred embodiments, the tissue dilator devices and methods of fabrication of tissue dilators are particularly suitable for use as external nasal dilators for supporting, stabilizing, and dilating nasal tissues adjacent and overlying nasal airway passages, including the nasal valve and/or the vestibule areas thereof.

BACKGROUND OF THE INVENTION

A portion of the human population has some malformation of the nasal passages which interferes with breathing, including deviated septa and swelling due to allergic reactions. A portion of the interior nasal passage wall may draw in during inhalation to substantially block the flow of air. Blockage of the nasal passages as a result of malformation, symptoms of the common cold or seasonal allergies are particularly uncomfortable at night, and can lead to sleep disturbances, irregularities and general discomfort.

Spring-based devices for dilating outer wall tissues of the human nose adjacent the nasal passages, and the use of resilient means to engage and urge outwardly the nasal passage outer walls from either the interior mucosa or exterior epidermis sides thereof, have a history spanning over one hundred years. Some examples of present external nasal dilators are disclosed in U.S. Pat. Nos. 6,453,901; D379,513; D429,332; D430,295; D432,652; D434,146; D437,64; U.S. patent application Ser. Nos. 08/855,103; 12/024,763; 12/106,289; and Japanese patent Reg. No. 1037944; the entire disclosures of which are incorporated by reference herein. The commercial success of at least one of these inventions, together with that of other modern external nasal dilators, collectively and commonly referred to as nasal strips, has led to the establishment of a nasal dilator product category in the consumer retail marketplace. Commercial success of prior art nasal dilator devices disclosed before 1990, in particular that of U.S. Pat. No. 1,292,083, and in the absence of evidence to the contrary, is presumed to be consistent with the consumer product environments at the times of those inventions.

A long-standing practice in the construction and use of medical devices which engage external bodily tissue (i.e., tissue dilators, nasal splints, ostomy devices, surgical drapes, etc.) is to interpose an interface material between the device and the user's skin to facilitate engagement of the device to the skin and to aid user comfort. Said material, such as a spunlaced polyester nonwoven fabric, typically has properties which permit limited, primarily plastic and somewhat elastic deformation within the thickness thereof. These properties can spread out peeling, separating or delaminating forces such as may be caused by: gravity acting on the weight of the device; the device's own spring biasing force or rigidity (such as that of a tissue dilator or nasal splint); biasing force that may be present in bodily tissue engaged by the device; surface configuration differences between the device and the skin of the device wearer; displacement of the device relative to the skin or external tissue as a result of shear, tensile, cleavage and/or peel forces imparted thereat via wearer movement (e.g., facial gestures) and/or contact with an object (e.g., clothing, pillow, bedding, etc.) that may cause partial or premature detachment of the device from the wearer. By spreading out these delaminating forces, said interface material acts as a buffering agent to prevent the transfer of said forces to its adhesive substance, if any, and thereby to the skin. Preventing the transfer of focused delaminating forces substantially eliminates any itching sensation (caused by the separation of the adhesive substance or device from the skin) that a wearer may experience if these delaminating forces were otherwise imparted directly to the skin.

External nasal dilators typically feature a functional element and an engagement element. The functional element consists of a metal or plastic member capable of resilient deformation such that when flexed it returns substantially to its initial, un-flexed, state. The engagement element typically consists of a flexible material with a pressure sensitive adhesive disposed on one side. Said material may further act as an interface buffer as described above. Adhesive may be used on the functional element to provide additional engagement means. The known nasal dilator art combines functional and engagement elements in a variety of configurations.

There has been a continuing need in the art to develop nasal dilators which address certain inherent limitations of the functional and engagement elements. These limitations include limited skin surface area adjacent the nasal passages, adhesive engagement vs. delaminating spring biasing forces, device comfort and durational longevity, and economical fabrication and assembly of dilator components.

Firstly, tissues associated with and adjacent the nasal passages have limited skin surface areas to which dilation may be applied. Said surfaces extend upward from the nostril opening to the cartilage just above the nasal valve, and extend outward from the bridge of the nose to each approximate line where the sides of the nose meet each cheek.

Secondly, nasal dilators are, of necessity, releasably engaged to outer wall tissues by use of pressure sensitive adhesives. Skin surfaces transmit moisture vapor to the surrounding atmosphere. The adhesives break down in the presence of skin oils, moisture and the transmission of moisture vapor, often within hours.

Thirdly, the functional element of modern nasal dilators is a flat, semi-rigid resilient member that is substantially rectangular or slightly arcuate in shape and made of thermoplastic resin. The resilient member is flexed across the bridge of the nose, extending over the nasal passages on each side of the bridge. When held thereto by the engagement element, the resilient member exerts a spring biasing force as it tries to return to its original, typically planar, state. The spring biasing force extends outward from the central portion of the device to the opposite end regions thereof, creating primarily peel forces at said end regions together with some tensile forces, which act to disengage the device from the skin surfaces.

To accommodate the average human nose, overall nasal dilator dimensions are typically from about 5.0 cm to 7.5 cm (2.0" to 3.0") in length and about 1.2 cm to 2.5 cm (0.5" to 1.0") in width. To produce from about 15 grams to about 30 grams of spring biasing force (enough to provide dilation or stabilization to nasal outer wall tissues without readily compromising the integrity of the engagement element), spring-based dilator device resilient members have dimensions from about 4.0 cm to about 6.0 cm (1.6" to 2.4") in length, and from about 0.61 cm to about 1.22 cm (0.24" to 0.48") in width, at a thickness of 0.18 mm or 0.25 mm (0.007" or 0.010"). A resilient member thickness other than 0.010" or 0.007" is not preferred in the art, but could be incorporated into device design with proportionate adjustments to width and length.

A portion of known nasal dilator art is suitable or adaptable for commercialization in the present consumer retail markets. Some of these have had commercial success, including devices disclosed in U.S. Pat. Nos. D379,513; 6,453,901; 5,533,503; 5,546,929; RE35408; 7,114,495 and certain devices based upon Spanish Utility Model 289-561 for Orthopaedic Adhesive. While these devices provide sufficient dilation of nasal passageway tissue and thus provide the claimed benefit to the vast majority of users, they are not configured to fully overcome the aforementioned limitations.

The functional and engagement elements of modern nasal dilator devices are manufactured without regard to integrating them efficiently. Based on approximate dimensions of 2.63"L×0.63"W (from typical overall dimensions stated above), commercially available nasal strip devices that are substantially rectangular in shape typically use about 1.66 square inches of material for the interface/engagement material layer, and up to about 3.31 square inches of material if both an interface layer and a cover material layer are used. The use of both layers has been a best practice. Nasal strips are typically manufactured in a continuous process, oriented parallel to the machine direction (MD) of the material used. Standard manufacturing (converting) technique typically spaces one device from another by about 0.125" on each side so that waste material can be removed as a single matrix. If finished dilators are to be individually packaged in the same operation, said spacing may be increased to about 0.19", or more, on all sides. This extra spacing provides a suitable contact perimeter extending around each dilator unit so that upper and lower packaging material webs may form an adequate seal to each other. Individual packaging is also considered a best practice for nasal strips available in the present retail market.

Nasal strips fabricated in closer proximity to each other, in order to reduce material waste, for example, are typically packaged individually in a separate operation. Of course a separate packaging operation has a corresponding additional cost. Dilator manufacturers typically weigh the cost of wasted material against the cost of a separate packaging operation.

Material waste from manufacturing dilator devices, excluding material for the engagement element, may approach that which is devoted to the dilator itself. For example, dilator devices fabricated (converted) in a spaced-apart relationship using about 1.66 square inches of material for each of two layers (engagement layer and cover layer, as described above) requires about 6.0" sq. of material total (2.63" dilator length plus 0.19" on each long side, multiplied by 0.63" dilator width plus 0.19" on each short side). Accordingly, 2×1.66" sq. devoted to the device itself out of 6" sq. of material is a usage-to-waste ratio of about 6:5, or about 55% material used to about 45% material wasted.

The usage-to-waste ratio of material used for the engagement element in dilator devices can range from as low as about 30%/70% to as high as about 67%/33% (where about 30% and 67% of the material, respectively, is devoted to the element itself) depending upon the dilator manufacturing technique used. Resilient members are typically formed from a continuous strip of material oriented parallel to the machine direction of the fabrication process. If the material strip is equal to the width of the finished resilient member, and the member extends to the lateral end edges of the finished dilator unit, there is a usage-to-waste ratio of about 2:1 (about 2" resilient member length plus spacing between successive lengthwise dilators equals about 3" total length). In this manner material waste is limited largely to the distance between successive dilator units fabricated lengthwise, end to end.

Dilator devices in which the resilient member is centered within the peripheral edges of the dilator (an "island placement" converting technique commonly used to simultaneously die cut and centrally register a component within the perimeter edges of a finished unit) may have as little as 30% of the material devoted to the resilient member element itself. In addition to the wasted material between successive dilator units fabricated lengthwise end to end, island placement typically requires an additional 0.125" of material width on each long side of the finished resilient member, so as to remove waste material as a single matrix from around successive spaced apart resilient members. While the finished resilient member width is 2" length×0.21" width, adding 0.125" of extra width on each long edge increases total width of resilient material strip to 0.46". Thus 1.38" sq. (3"×0.46") of resilient element material is used to fabricate and position a 0.42" sq. (2"×0.21") resilient member; a usage-to-waste ratio of about 1:2.

It should be noted that the material waste described above does not include that from machine set-up and calibrating, or that from the pre-converting of materials as supplied by their respective manufacturers. However, even minor efficiencies can provide a competitive advantage and improve dilator manufacturers' value propositions in a consumer product retail environment. Based on the dimensions of dilator engagement and functional elements as described above, the embodiments of the present invention are conducive to material usage/waste of about 80%/20% or better for the resilient and base layer materials (about a 4:1 ratio), and about 75%/25% for the cover layer material (about a 3:1 ratio).

Nasal dilator devices heretofore available in the consumer marketplace feature a symmetric resilient member or members. That is, each horizontal half of each member (extending onto opposing nasal outer wall tissues) is the mirror image of the other. Where there are two resilient members disclosed in the prior art, each member is fabricated to identical or similar dimensions. Uniform resilient members are generally more economical to mass produce. The present invention illustrates that non-identical and asymmetric resilient members may be fabricated with equal or greater efficiency as their symmetric counterparts, at the same or lower cost.

U.S. Pat. No. 6,453,901 discloses a manufacturing method of forming a strip of identical web-connected resilient members from an elongated material sheet, laminating the strip to strips of base layer and cover layer material, and die cutting the laminate on predetermined lines to form successive nasal dilators with their lengths oriented perpendicular to the machine direction of the fabrication process. Material between the web-connected resilient members and finished dilators is wasted. Accordingly, the '901 disclosure does not teach this technique as a manufacturing efficiency, but rather as an alternative process to the traditional lengthwise, end-to-end, fabrication methods described above, and further as a means to form complex resilient member structures. The present invention builds upon the '901 disclosure by illustrating methods whereby to form complex resilient member structures while limiting waste material and improving manufacturing efficiency.

In the modern consumer product market, nasal dilator innovation and competitive value propositions to resellers and consumers have been limited. Accordingly, there is a need in the art for both nasal dilator innovation and premium quality dilator devices at lower costs. The present invention is directed to discrete embodiments and various forms of external nasal dilators, including techniques and methods for manufacturing finished dilator units and their constituent elements, members and components.

SUMMARY OF THE INVENTION

The present invention teaches, depicts, enables, illustrates, describes and claims new, useful and non-obvious apparatus and methods of dilating external tissue. The present invention provides a variety of tissue dilators adapted to engage an exterior tissue region of a nose to dilate the nasal passages thereof, including methods of manufacturing tissue dilators. More particularly, the present invention provides novel methods of efficiently fabricating functional elements of tissue dilators on a mass scale. The present invention builds upon the prior art and addresses still unmet needs in the art.

The external nasal dilator of the present invention comprises a laminate of vertically stacked material layers. The laminate is held together by an adhesive substance disposed on at least one flat surface side of at least one of its constituent layers. The laminate forms a unitary, or single body, truss. Each layer includes one or more members, and a member may further include one or more components. The truss features horizontal regions, including first and second end regions adapted to engage outer wall tissues of first and second nasal passages, respectively, and an intermediate region adapted to traverse a portion of a nose located between the first and second nasal passages and joining the end regions. In use the dilator acts to stabilize and/or expand the nasal outer wall tissues and prevent said tissues from drawing inward during breathing. The truss is configured to be comfortable on the tissue engaged and to be easily removed from the tissue with little or no stress thereto.

The dilator is die cut from a laminate of separate materials. Dilator layers or members may be die cut, in whole or part, from one or more individual materials before or during assembly of the laminate. Methods of manufacture include separate functions, or steps, for the fabrication and assembly of dilator elements, and the packaging of finished dilator units individually or in groups.

Embodiments of the present invention include, without limitation, new and non-obvious means to efficiently manufacture with minimal waste nasal dilator devices and the constituent layers, members and components thereof. Preferred embodiments also include methods for simultaneously fabricating identical, non-identical, symmetric or asymmetric dilator members, components thereof, and finished nasal dilator devices with equal efficiency and with at the same or lower cost as traditional methods. Embodiments further include: means to assist centering on the nose of a wearer comprising a separation, projection or other index marker located at the intermediate region of the dilator; a resilient member or component thereof having a gradiently reduced width; dilator layers, members or components made from materials which are transparent or translucent; and means for incorporating promotional printing and/or contrasting colors (such as team sports colors) into the dilator fabrication process.

It is the principal objective of this invention to provide nasal dilator devices which overcome the aforementioned limitations and disadvantages of prior dilator devices. A more specific objective of the present invention is to provide nasal dilators and methods of manufacture that minimize material waste and reduce traditional manufacturing cost by configuring device layers and/or members to be fabricated, in whole or part, along common lines or edges that simultaneously define at least a portion of their peripheral dimensions while establishing a spaced apart relationship therebetween without sacrificing usable material to do so. A further objective of this invention is to provide nasal dilator devices that are configured to allow their constituent layers to be fabricated so as to return a greater number of individual dilator units, layers, members or components thereof per a given quantity of material, and/or to maximize the percentage of a given quantity of raw material used in the fabrication process.

A still further objective of this invention is to provide nasal dilator devices that are less expensive to manufacture, that utilize manufacturing techniques that create efficiencies and utilize less material without increasing fabrication and assembly costs, that use less expensive materials, that use less overall material in device construction, that are simple and easy to use, that effectively dilate external tissue, that provide a gradiently reduced spring biasing force extending from the intermediate region to at least a portion of at least one end region of the dilator, that provide disparate spring biasing force to opposing nasal passages, and that are more affordable to the user than prior art dilator devices.

For fabricating and assembling the embodiments of the present invention, the skilled man in the art will appreciate the applicability of the continually developing art of medical device converting, including rotary laminating and die cutting, flat-bed and class A tool die cutting and punching, fluid or pneumatic modular automation systems, pneumatic feeding and material handling components and systems, and the application of electronic or computerized controls thereto.

The present invention is not limited to the illustrated or described embodiments as these are intended to assist the reader in understanding the subject matter of the invention. The preferred embodiments are examples of forms of the invention comprehended by that which is taught, enabled, described, illustrated and claimed herein. All structures and methods which embody similar functionality are intended to be covered hereby. In certain instances, the devices depicted, taught, enabled and disclosed herein represent families of new, useful and non-obvious tissue dilators having a variety of alternate embodiments. The skilled man will further appreciate that features, devices, elements, components, methods, processes or techniques may be applied, interchanged or combined from one embodiment to another. Dilator layers, members, components, materials, or regions may be of differing size, area, thickness, length, width or shape than that illustrated or described while still remaining within the purview and scope of the present invention. The preferred embodiments include, without limitation, the following numbered, discrete forms of the invention, as more fully described below.

In the specification and claims herein, the term vertical refers to a direction parallel to the thickness of the dilator or truss. The term horizontal refers to a direction parallel to the length, or longitudinal extent, or long axis of the dilator or truss. The term lateral refers to the width or opposite end edges of the dilator or truss, or a direction perpendicular to the length, longitudinal extent, or long axis of the dilator or truss. The term longitudinal centerline refers to a line parallel to the longitudinal extent of the dilator or truss, bisecting the width of the dilator or truss midway between its upper and lower long edges. The term lateral centerline refers to a line perpendicular to the length, longitudinal extent, or long axis of the dilator or truss, bisecting the long axis, or upper and lower long edges, midway along the length thereof.

BRIEF DESCRIPTION OF THE SEVERAL VIEWS OF THE DRAWING

In the drawings which accompany this disclosure, like objects are referred to with common reference numerals. Drawings are not rendered to scale.

FIG. 10 is a perspective view of a form of nasal dilator embodying features of the present invention.

FIG. 11 is a fragmentary plan view illustrating the steps of a method to manufacture the nasal dilator of FIG. 10.

FIGS. 17a-17c are fragmentary plan views of a manufacturing method embodying features of the present invention.

FIG. 20 is a fragmentary exploded perspective view illustrating the intermediate and final steps of a manufacturing method begun in FIG. 17a.

DETAILED DESCRIPTION OF THE INVENTION

Figure 1:
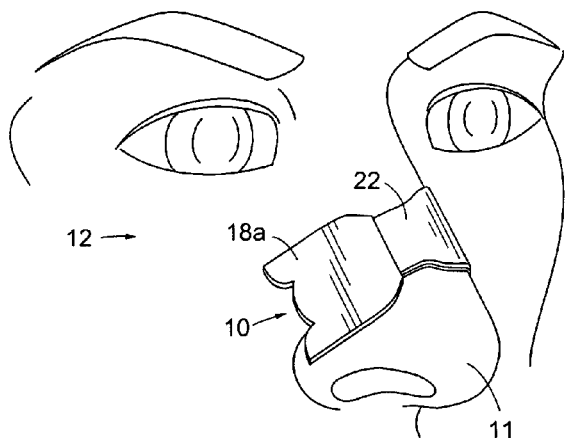
FIG. 1 is a perspective view of a portion of a face with a nasal dilator in accordance with the present invention secured to the nose of a wearer.

An embodiment of a nasal dilator, 10, in accordance with the present invention, is illustrated in FIG. 1 which shows dilator 10 engaged to a nose, 11, seen as a portion of a human face, 12.

Figure 2:
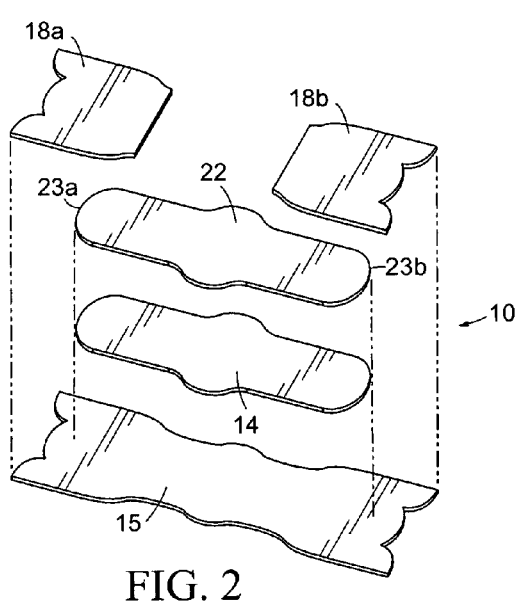
FIG. 2 is an exploded perspective view of the nasal dilator of FIG. 1.

As seen in FIG. 2, dilator 10 comprises a laminate of vertically stacked material layers. Said layers comprise a base layer having at least one base member, 14, a resilient layer comprised of at least one resilient member, 22, and a cover layer composed of cover members, 18a and 18b. The layers may be laminated to each other by any suitable means including heat or pressure bonding, but are preferably laminated by an adhesive substance disposed on at least one flat surface side of each thereof. Cover members 18a and 18b are dimensionally configured to correspond to at least portions of the skin surfaces of outer wall tissues adjacent first and second nasal passages, respectively. The cover and/or base layers serve as the primary engagement element while the resilient layer provides the functional element of dilator 10. A protective release paper liner, 15, removably covers exposed adhesive from the base, resilient or cover layers preliminary to use of dilator 10 on a nose of a wearer. The shape and dimensions of release liner 15 may correspond to the periphery of dilator 10 or may exceed the periphery one or more dilators 10. Where protective liner 15 corresponds to the periphery of dilator 10, it may be bisected laterally to form two parts, which may overlap, to facilitate removal from the dilator preliminary to use. Though not required, the layers or constituent members of dilator 10 are preferably aligned along their longitudinal centerlines.

The preferred material for the base and cover layers is from a group of widely available flexible nonwoven synthetic fabrics that allow the skin on user nose 11 to exchange gases with the atmosphere and to maximize comfort of dilator 10 thereon. Alternatively, any suitable fabric or plastic film may be used. Preferred materials may be obtained from medical device material manufacturers and are typically available in colors of white, various shades of tan or beige, and transparent. A pressure sensitive adhesive substance is disposed on at least one flat surface side of said material, which is the adhesive side, opposite the non-adhesive side. (The non-adhesive side is typically opposite the skin engaging side.) The adhesive is preferably of a type that is biocompatible with external human tissue for engaging dilator 10 to the nose 11 of a wearer. A protective layer of release paper liner covers said adhesive. The preferred materials are typically available in rolls wound in a machine direction (MD) or warp, which is perpendicular to the cross direction (XD) or fill, of the material. The base and cover layers of dilator 10 may be fabricated parallel to either the warp or fill.

The preferred material for resilient member 22 is a biaxially oriented polyester resin (PET). PET has suitable spring biasing properties and is widely available under trade names such as Mylar® and Melinex® in standard thickness of 0.005", 0.007", and 0.010". PET is typically transparent, but may also be translucent or opaque. In the alternative, any thermoplastic material having suitable resilient properties may be used. The preferred material may have a pressure sensitive adhesive disposed on one surface, with said adhesive protected by a release paper liner until the material is used. PET, in particular, may be printed on one or both surfaces using conventional printing means. The spring biasing properties of PET are similar both MD and XD. The resilient members of the embodiments of the present invention are preferably fabricated from an elongated sheet, typically wound into a roll, of PET material which comes in standard thickness of 0.007" and 0.010".

Resilient member 22 is configured by its overall shape and dimensions of width and length relative to the thickness of the resilient material used to provide suitable spring return biasing force as discussed hereinbefore. Resilient member 22 preferably has an adhesive substance disposed on at least a portion of at least one of two opposite flat surface sides for engaging nasal outer wall tissues and/or laminating it to other layers of dilator 10. As further seen in FIG. 2, resilient member 22 has opposite end edges, 23a and 23b, respectively, that may conform or correspond, at least in part, to portions of end edges of the base or cover layers of dilator 10.

Figure 3:
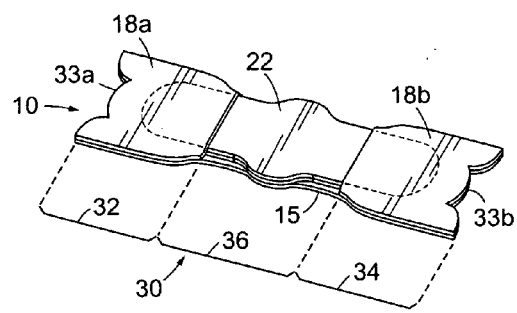
FIG. 3 is a perspective view of the nasal dilator of FIG. 2.
Figure 4:
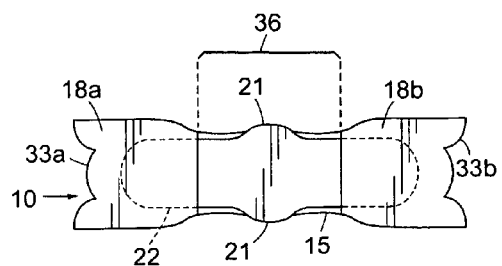
FIG. 4 is a plan view of the nasal dilator of FIG. 3.

The members which make up the base and cover layers of dilator 10 may have either identical or dissimilar dimensions or peripheries, in whole or in part, compared to each other. Their respective shapes may be symmetric or asymmetric, and also may be of like or dissimilar size or scale. The peripheral edges of dilator 10 may be defined by a single layer or, as shown in FIGS. 2-4, by a combination of two or more of its layers. The width or length of dilator 10 may be defined by the base layer, cover layer, or both, and portions of one or more layers may engage the skin simultaneously. The base and cover layers of dilator 10 may be interchanged. The periphery of the base layer may match the periphery of the resilient layer. Portions of one or both flat surfaces of one layer overlap a portion or portions of another layer. However, when engaged on the nose of a wearer, preferably no portion of a layer or member extends substantially beyond those skin surface areas associated with the nasal outer wall tissues as described hereinbefore. In addition, either the base layer or cover layer may be optionally eliminated in whole or in part. Preferably, however, at least a portion of one flat surface of the base or cover layer is laminated to one of two flat surfaces of the resilient layer.

As illustrated in FIG. 3, the laminated layers of dilator 10 form a unitary, or single body, truss, 30, having horizontal regions indicated approximately by broken lines. Truss 30 includes a first end region, 32, a second end region, 34, and an intermediate region, 36, joining first end region 32 to second end region 34. The layers, members or components of dilator 10 may overlap from the originating region to the adjacent region. End regions 32 and 34 are adapted to engage outer wall tissues of first and second nasal passages respectively, and further include lateral end edges, 33a, and 33b, respectively, which also define the outer lateral end edges of truss 30 and thus dilator 10. The respective widths and lengths of end regions 32 and 34 are defined, at least in part, by the base and/or cover layers of dilator 10. The width of intermediate region 36 is preferably less than the width of end regions 32 and 34 and may be defined by any layer or combination of layers.

As seen in FIG. 4, intermediate region 36 includes a material separation, 21, located along the upper and/or lower long edges of intermediate region 36. Material separation 21 may be in the form of a notch, protrusion, indentation or the like, depending on its use and purpose. In the present embodiment separation 21 is meant to be aligned with the bridge of the nose by the user so as to distribute the spring biasing force of dilator 10 to opposing nasal passages (equally, if separation 21 is located on the lateral centerline of dilator 10, or unequally if located to one side or the other of the centerline within intermediate region 36). Material separation 21 may further be configured to affect the functional element of dilator 10, depending upon its size and shape as well as its location. By protruding outward or inward from intermediate region 36, for example, material separation 21 may increase or decrease, respectively, the spring biasing properties of resilient member 22.

When engaged to a nose 11, dilator 10, through its resilient means as a result of its constituent layers and members combined to form truss 30, acts to stabilize and/or expand the nasal outer wall tissues and prevent said tissues from drawing inward during breathing.

Figure 5:
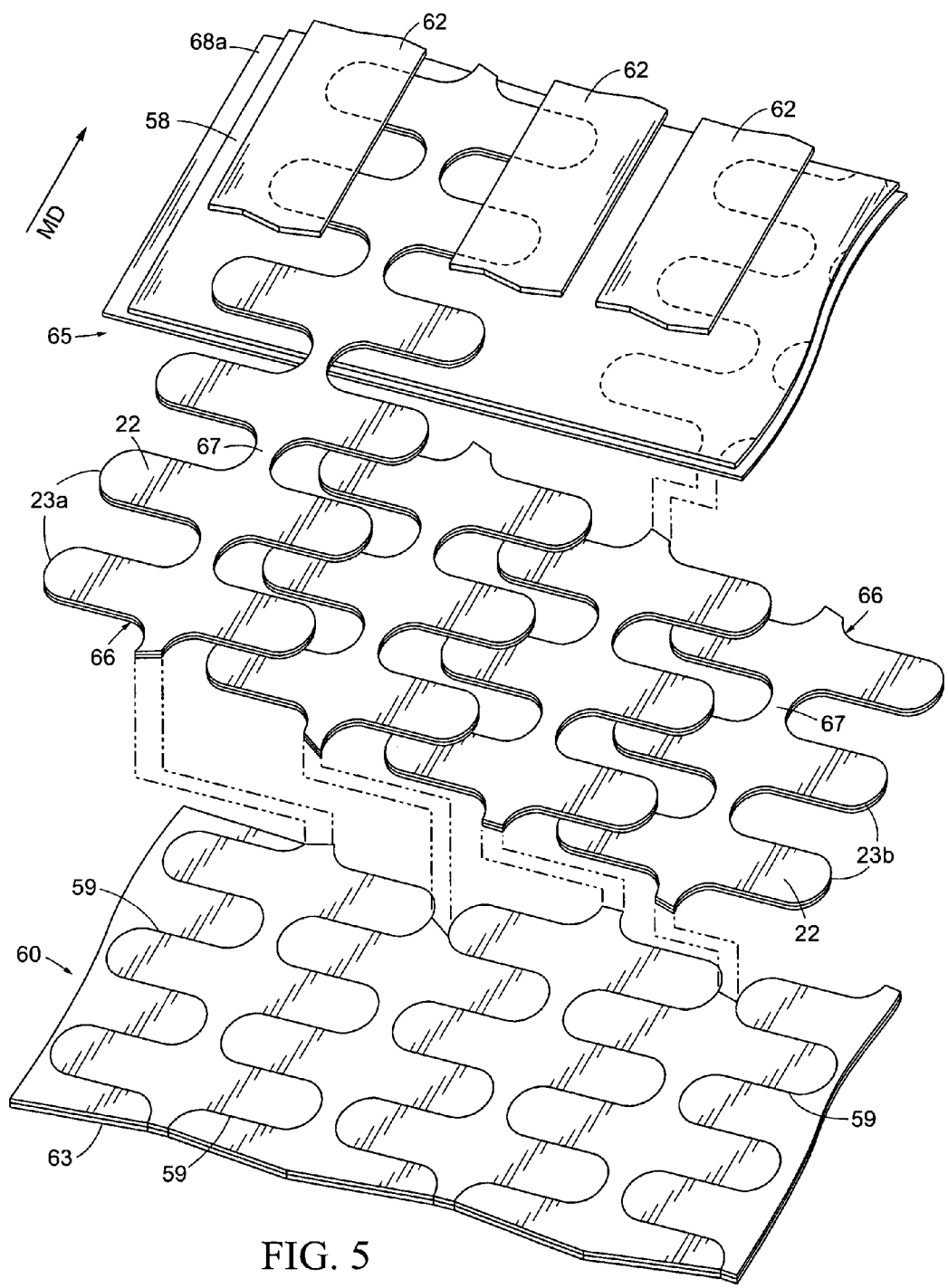
FIG. 5 is a fragmentary exploded perspective view illustrating the initial steps of a method to manufacture the nasal dilator of the present invention.

FIGS. 5-9 illustrate the steps of a manufacturing method to produce dilator devices of the present invention. Successive finished dilator units 10 are die cut along prescribed lines from a laminate of material layers. The process renders individual dilators 10 in spaced apart relationship sealed between two webs of packaging material. FIG. 5 illustrates the initial manufacturing steps where successive interconnected resilient members 22 are die cut from an elongated or continuous sheet of suitable resilient layer material, 60, along prescribed cut lines, 59, using a continuous cutting process. A plurality of successive individual resilient members 22 are interconnected by webs, 67, which integrate them into an elongated or continuous strip, 66. Cut lines 59 form a plurality of strips 66 nested along common lines adjacent each other in a repeating pattern. The repetition of the pattern is limited only by the physical dimensions of the resilient layer material.

Resilient layer material 60 may include a preferred base layer material, 63, laminated thereto, from the adhesive side of material 60 to one side of material 63. Material 63 in turn preferably has an adhesive substance disposed on the opposite side thereof protected by a release paper liner as described hereinbefore. Cut lines 59 extend vertically through resilient layer material 60 and base layer material 63 to form adjacent nested strips 66 further including interconnected base members 14 together with resilient members 22 of dilator 10 (as illustrated in FIG. 2). To facilitate mass production, cut lines 59 may extend through the protective release paper liner of material 60 to allow one or more strips 66 to be re-wound or coiled.

As discussed hereinbefore, resilient member 22 is configured by its width, length and thickness to provide suitable spring return biasing force to effectively dilate nasal outer wall tissues. The dimensions of interconnected resilient members 22 of strip 66 may be configured to any size or shape that falls within these parameters. Cut lines 59 define each horizontal half of each interconnected resilient member of strip 66, each half comprising upper and lower long edges and an end edge, 23a or 23b. The edges of interconnecting web 67 are formed on a common line with the end edges of adjacent interconnected resilient members on each side thereof. The length of interconnecting web 67 defines the distance between successive resilient members within strip 66; its length thus further corresponds to the width of the resilient member adjacent each side thereto, and said width thus defines the spaced apart relationship between resilient members nested adjacent thereto.

It will be obvious to the skilled medical device converter that the continuous cutting process shown with respect to FIG. 5 is appropriate to rotary and flat-bed die cutting. It will be further obvious that a portion of the resilient material 60 is wasted along two outside edges thereof. Each waste portion corresponds approximately to one long half of strip 66. Accordingly, the wider the material 60 matrix, the greater number of whole strips 66 yielded in proportion to the two outside waste portions. A material width of up to about 9" is commonly used in a rotary die-cutting press, while flat-bed die cutting presses can accommodate greater widths. The latter is thus conducive to a greater yield ratio, while the former may be more conducive to continuous material feed.

Strip 66 is preferably formed parallel to the machine direction (MD) of resilient material 60, with said interconnected resilient members formed perpendicular thereto. Said machine direction is indicated in the drawings herein by a directional arrow and the notation, "MD". However, nested strips 66 may be optionally die cut XD, or perpendicular to the machine direction, with the lengths of the interconnected resilient members parallel to the machine direction. Strip 66 would thus extend from one long edge of material 60 to the opposite edge. This arrangement is conducive, for example, to "sheet feed" where successive sheets of material 60 are fed into a press, such as with a flat bed die cutting system.

Continuing on with respect to FIG. 5, elongated strips 66 are separated from the material 60 matrix. One or more strips 66 are layered onto a separate elongated or continuous sheet of release paper liner material, 58, which in turn is layered onto one of two elongated or continuous packaging material webs, 68a. Strips of a preferred cover layer material, 62, are layered on top of the laminate consisting of web 68a, release liner 58 and strip 66, and positioned substantially over where the respective end regions of dilator 10 will be formed. Material strips 62 are laminated via their adhesive sides to the non-adhesive side of strip 66 and in between interconnected resilient members to paper liner 58, thus forming a fabrication matrix, 65, from which finished nasal dilators 10 will be die cut. Packaging material web 68a forms the foundation of fabrication matrix 65, providing the surface against which dilators 10 are die cut using the well known kiss-cut technique.

FIG. 5 shows that release paper liner 58 is wider than one or more strips 66. (In turn, packaging web 68a is wider than liner 58.) The skilled converter will see that if cut lines 59 extend through the release paper liner protecting the adhesive substance disposed on material 60, and thus is included in each strip 66, said liner must be removed before layering strip 66 onto the new liner material 58. As noted previously, leaving the paper liner on each strip 66 allows one or more of the strips to be recoiled as desired. In the alternative, strips 66 may be kiss cut against the paper liner protecting the adhesive on material 60, provided that immediately after separation from the material 60 matrix, each strip 66 is layered onto a new paper liner 58 as described above. Removing one or more of said kiss cut strips 66 (every other one, or one in three, two in four, etc.), for example, allows the converter to slit, recoil and reuse the release liner left behind (said liner having served to cover the adhesive disposed on resilient material 60/base layer material 63). Release paper liner is inexpensive compared to the cost of resilient, base and cover layer materials.

Figure 6:
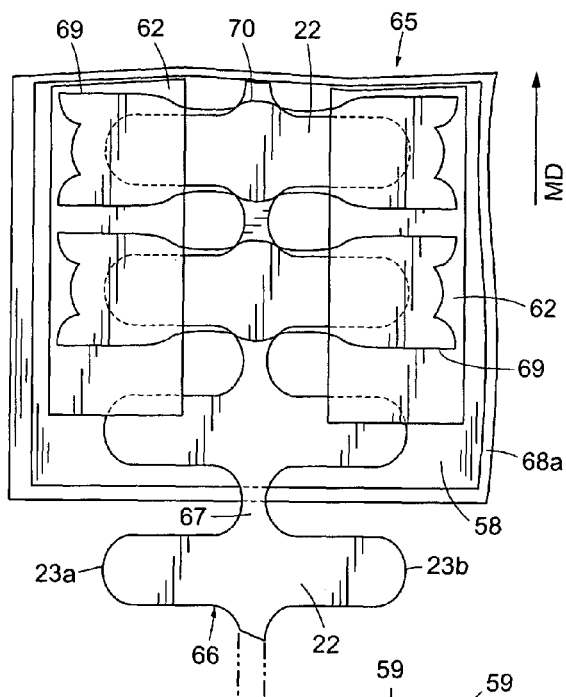
FIG. 6 is a fragmentary plan view further illustrating the steps shown in FIG. 5.
Figure 6:
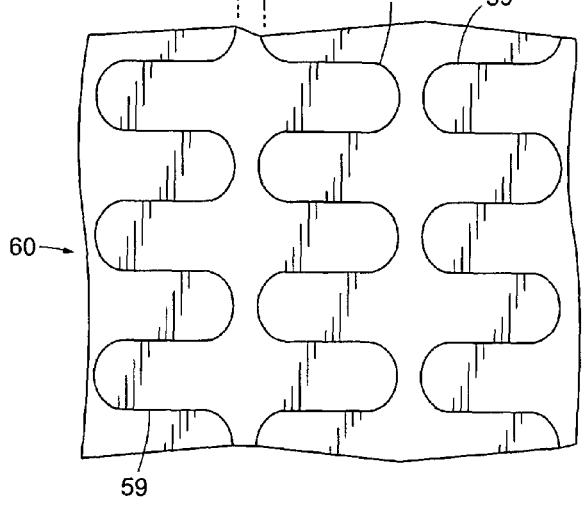

FIG. 6 illustrates a subsequent step in which die cut lines, 69, extend vertically through fabrication matrix 65 to, but not through, packaging web 68a so as to form individual dilators 10 suitably spaced apart such that upper and lower packaging webs may form a seal therebetween. Die cut lines 69 extend around each resilient member, adjacent thereto and as close as practicable to portions of the upper and lower long edges thereof, forming portions of the upper and lower long edges of release paper liner 15. Die cut lines 69 also define the long edges and lateral outside edges of cover members 18a and 18b. A section of die cut line 69, cut line portion 70, intersects strip 66 and severs each interconnecting web 67 to form upper and lower material separations 21 as more closely illustrated in FIG. 7. It should be noted that for manufacturing purposes, material separation 21 serves primarily as a connection/separation point between web 67 and resilient member 22. In this regard, separation 21 may be formed as an indentation, protruding inward or outward as little as possible. Locating web 67 along intermediate region 36 allows cut line portion 70 to form separation 21 as an index marker for aligning dilator 10 to the nose of a wearer and/or to serve as part of the functional element of the dilator.

FIG. 6 further illustrates that the respective widths of material strips 62 are uniform and define the respective lengths of cover members 18a and 18b. However, said widths and the spacing therebetween may be varying, constant or gradient. The inside edge of cover layer material 62 defines that portion of the inside lateral edges of cover members 18a and 18b not otherwise formed by die cut lines 69. The outside edge of material strip 62 may optionally correspond to all or part of lateral end edges 33a or 33b of truss 30.

It will be obvious to the skilled man in the art that a single cover layer material strip 62 may be used to span the width of strip 66. Two spaced apart cover layers 62 requires less material and lowers the cost thereof; and cover member material is thus applied to substantially to end regions 32 and 34 of truss 30 where it is needed most. Material economy notwithstanding, an additional cover layer strip 62 may be optionally laminated to strip 66, whereby to provide greater rigidity to laminate 65, or otherwise provide greater engagement element area to dilator 10.

Figure 7:
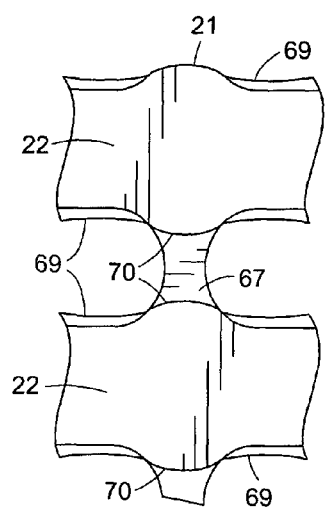
FIG. 7 is a fragmentary plan view, on an enlarged scale, illustrating placement of die cut lines illustrated in FIG. 6.

FIG. 7 more particularly illustrates web 67 severed by cut line portion 70 of die cut line 69 to form material separation 21 as a protrusion. Cut line portion 70 is preferably slightly wider than web 67 so as to avoid the formation of sharp corners thereabout.

Figure 8:
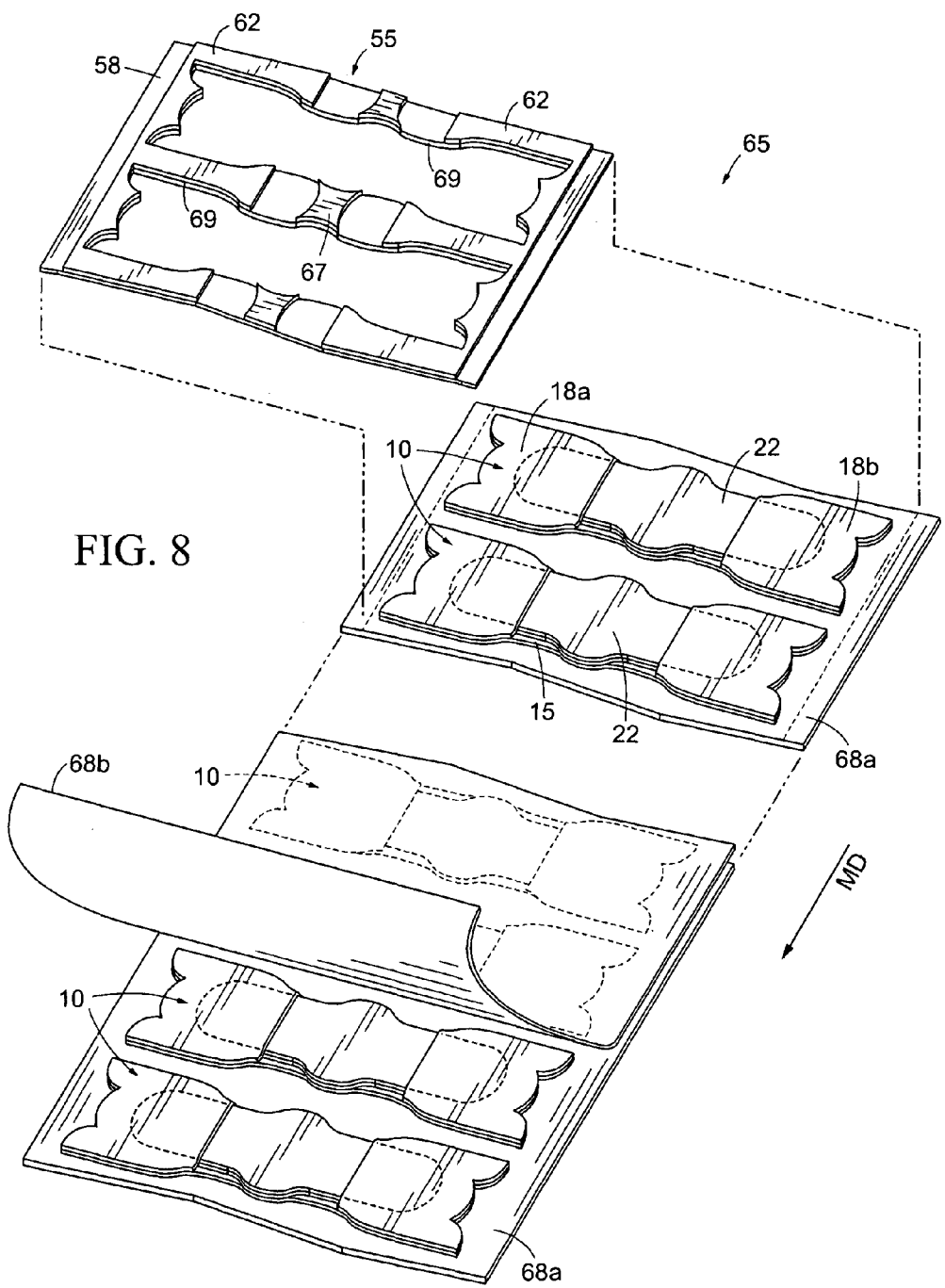
FIG. 8 is a fragmentary, exploded, perspective view illustrating the final steps of the manufacturing process illustrated in FIGS. 5-7.

FIG. 8 illustrates the final steps in which an elongated waste material matrix, 55, is separated from fabrication matrix 65. Waste matrix 55 includes portions of cover layer material 62 and interconnecting webs 67 removably adhered to paper liner 58. Removing waste matrix 55 leaves individual dilators 10 registered in a spaced apart relationship upon packaging web 68a. The second of two packaging webs, 68b, is then layered thereon, forming a seal with packaging web 68a around and between one or more individual dilators 10 so as to encapsulate the dilators therebetween. The sealed packaging webs may be bisected into sections of one or more dilators 10, as desired for retail sale.

FIGS. 5-8 illustrate strips 66 nested together along common lines, and base member 14 confined in size to that of the resilient layer, and cover members 18a and 18b confined substantially to end regions 32 and 34 of truss 30. Based on dilator engagement element and functional element dimensions described hereinbefore, this dilator device structure and its manufacturing method are conducive to material usage/waste of about 80%/20% or better for the resilient and base layer materials (about a 4:1 ratio), and about 75%/25% for the cover layer material (about a 3:1 ratio).

Figure 9:
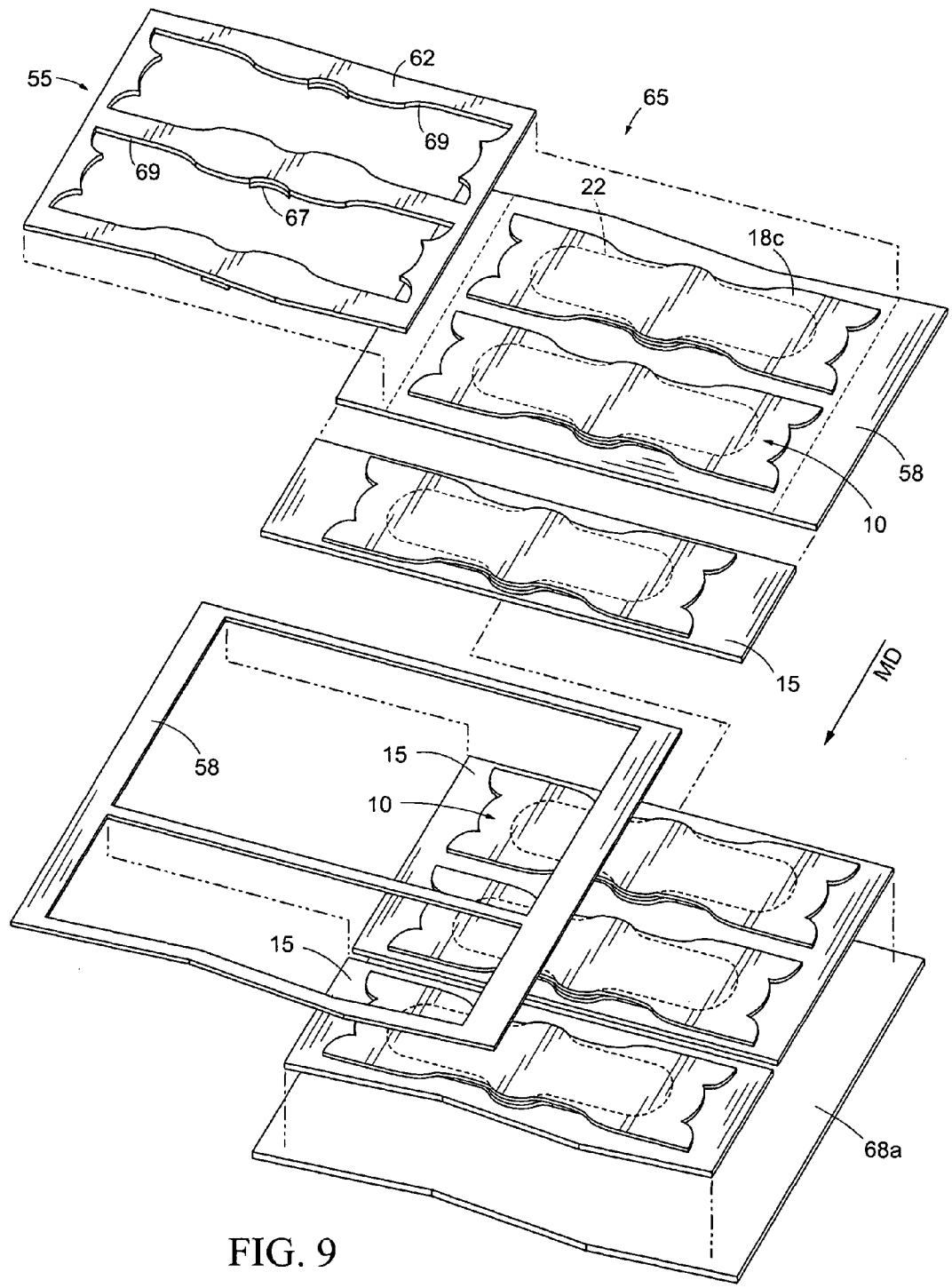
FIG. 9 is a fragmentary, exploded, perspective view illustrating alternate final steps to that shown in FIG. 8.

FIG. 9 illustrates an alternative fabrication step to that of FIG. 8. A single cover layer material strip 62 is used over strip 66 instead of two spaced apart strips. Die cut lines 69 extend vertically through fabrication matrix 65 to, but not through, release paper liner 58 by the aforementioned kiss-cut technique, leaving spaced apart individual dilators 10 releasably secured to liner 58 instead of to packaging web 68a. Waste matrix 55 is separated as a single continuous matrix by virtue that cover layer material 62 is wider than strip 66. Paper liner 58 may be bisected between one or more dilators 10, or may be die cut around one or more dilators 10 separating them into sections. In either case, release liner 15 thus has a periphery exceeding one or more dilators 10 as noted hereinbefore. Said sections may further be sealed between packaging material webs 68a and 68b.

FIGS. 10-13 illustrate an embodiment of dilator 10 and manufacturing method in accordance with the present invention. FIG. 10 shows resilient member 22 exposed on top of the base layer of dilator 10 and having gradient upper and lower long edges. One or both of the flat surfaces of resilient member 22 may be decorated, colored or imprinted.

FIG. 11 shows elongated strips 66 die cut from resilient layer material 60 along cut lines 59 as described hereinbefore. In this embodiment, however, material 60 does not include a base layer material laminated thereto. Cut lines 59 form tapered upper and lower long edges of interconnected resilient members, wider at the intersection of interconnecting web 67 and narrower at end edges 23a and 23b. The gradients are shown equal on each horizontal half of each resilient member, but cut lines 59 may form unequal gradients in material 60, so as to provide disparate spring biasing force to opposing nasal passages. Any coloring, imprinting, graphics or the like may be applied using conventional means to either flat surface side of resilient material 60 before adhesive is applied thereto, or to the non-adhesive side of material 60 either before or after forming nested strips 66.

To form fabrication matrix 65 and produce finished dilators 10, elongated strips 66 are separated from the material 60 matrix, as described hereinbefore, and layered on top of an elongated strip of base layer material 63. Material 63 is wider than strip 66 and includes protective release paper liner 58 covering its adhesive side. In turn, paper liner 58 is wider than material 63. Die cut lines 69 extend vertically through the entirety of fabrication matrix 65 to define the peripheral dimensions of adjacent dilators 10. One or more undercuts, backscore 52, are made vertically through release liner 58 from underneath. Die cut lines 69 also sever interconnecting webs 67 along cut line portions 70 as more particularly illustrated in FIG. 12. Base layer 14 thus defines the peripheral dimensions of truss 30, leaving resilient member 22 visible at the top of the vertical stacking order of the respective layers of dilator 10. FIG. 11 further illustrates that portions of upper and lower long edges of adjacent dilators 10 are formed along common die cut lines 69 corresponding approximately to the respective lengths of end regions 32 and 34. Die cut lines 69 also form the lateral end edges of dilator 10 in continuous succession just inside of, and adjacent to, the opposite outside edges of base layer material 63.

Figure 12:
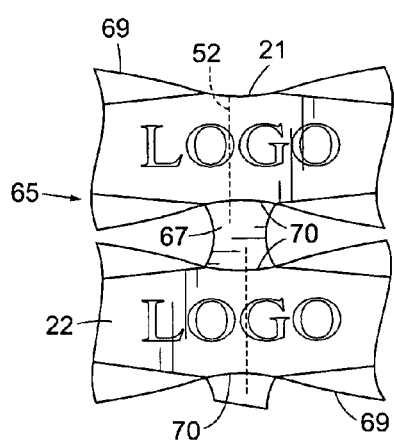
FIG. 12 is a fragmentary plan view, on an enlarged scale, illustrating placement of die cut lines illustrated in FIG. 11.

FIG. 12 more particularly illustrates that backscore 52 extends across where interconnecting web 67 is severed by cut line portions 70 to form material separation 21. Backscore 52 thus extends across what will be the width of release liner 15 at or near the lateral centerline of dilator 10 so as to facilitate removal thereof by a user. (The skilled man will note that the dilator of FIGS. 2-4 does not include a backscore as described here because release liner 15 extends slightly beyond a portion of the upper and lower long edges of dilator 10, providing a lip thereat that a user can easily grasp to separate the dilator from its protective liner prior to use.) Cut line portion 70 forms separation 21 as an indentation, preferably slightly wider than web 67 so as to avoid the formation of sharp corners thereabout and blended into the contour of die cut lines 69 which form the upper and lower long edges of dilator 10. The upper and lower long edges of dilator 10 thus converge with upper and lower long edges of resilient member 22 along cut line 70. The lateral extent, or depth, of separation 21 may be configured to affect the functional element of dilator 10 as discussed hereinbefore.

Figure 13:
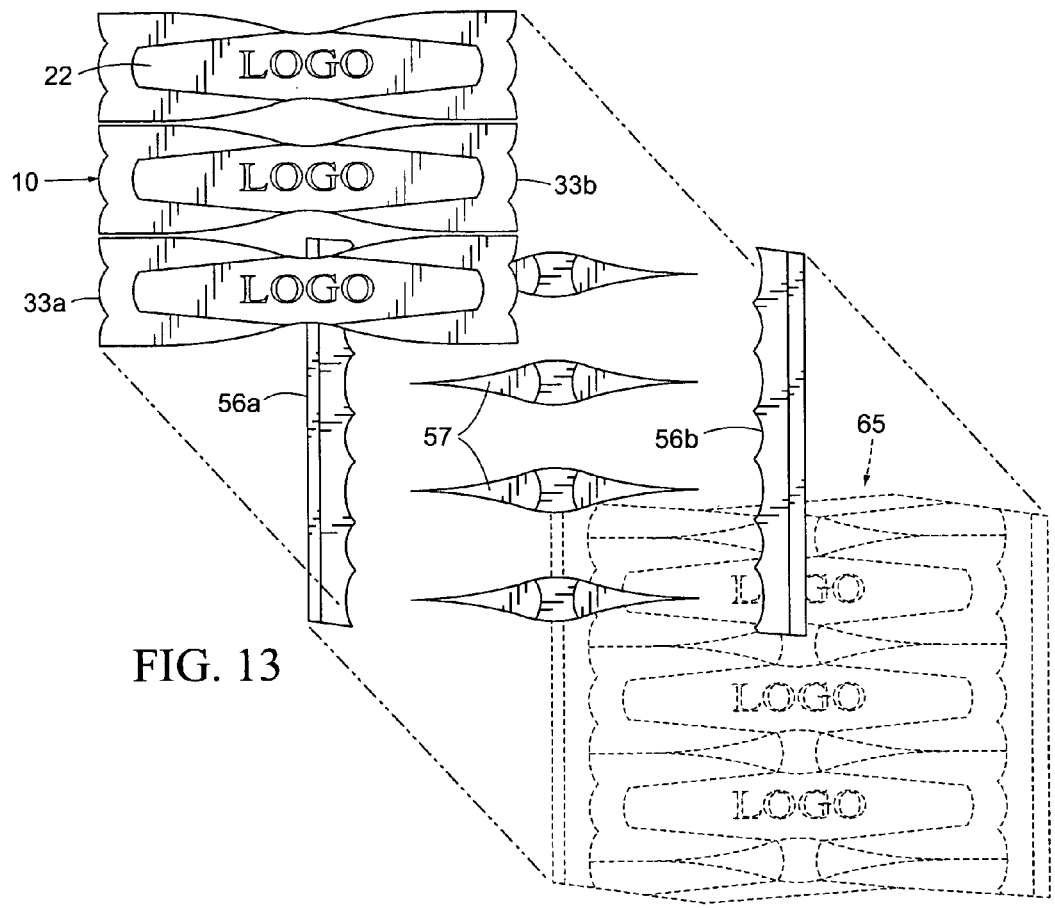
FIG. 13 is a fragmentary exploded plan view illustrating the step of separating finished dilator units from waste material relative to the manufacturing method of FIGS. 11-12.

As seen in FIG. 13, die cut lines 69 form portions of dilator upper and lower long edges on a common line. Fabrication matrix 65 is thus separated into a plurality of loose finished dilator units and waste pieces; the latter consisting of two elongated outside waste pieces, 56a and 56b, and individual center waste pieces, 57. The inside edge of waste pieces 56a and 56b are formed by the outside edges of fabrication matrix 65 and portions of die cut lines 69 which form end edges 33a and 33b. Waste pieces 56a and 56b may be re-wound, while waste pieces 57 may be punched through or suctioned from matrix 65 and collected. The resultant plurality of finished individual nasal dilators 10 are then captured in bulk. It should be noted that die cut lines 69 may optionally form some dilators along common upper and lower edges, and some in a spaced apart relationship as illustrated previously, in which case outside waste pieces 56a and 56b would interconnect with certain of center waste pieces to form a waste matrix.

Based on dilator engagement element and functional element dimensions described hereinbefore, the nasal dilator and manufacturing method of FIGS. 10-13 are conducive to material usage/waste of about 80%/20% for both the resilient layer base layer materials (about a 4:1 ratio).

Figure 14B:
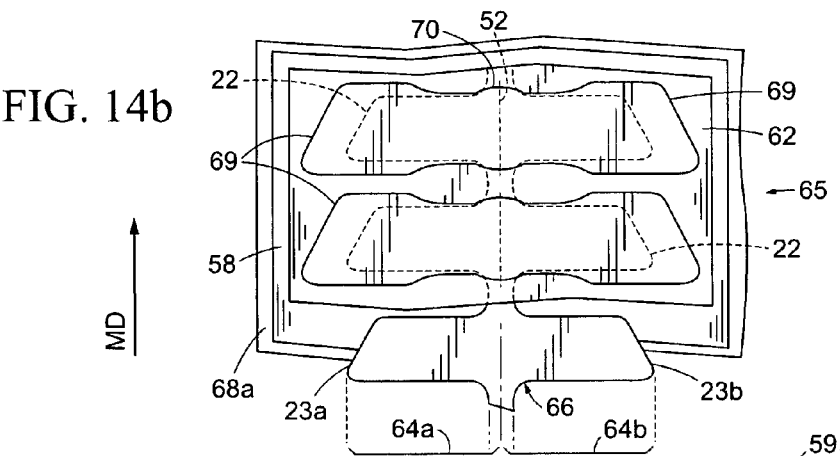
FIGS. 14a-14c are fragmentary plan views of a manufacturing method embodying features of the present invention.
Figure 14A:
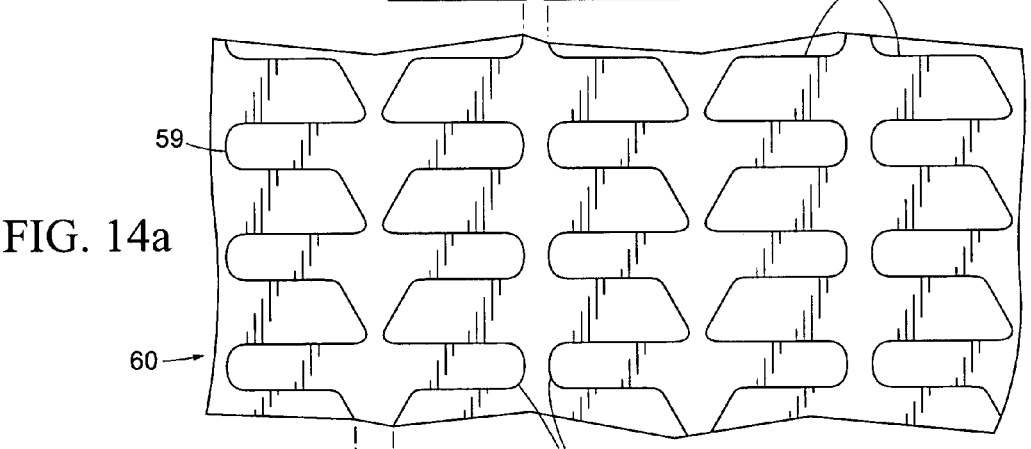
Figure 22:
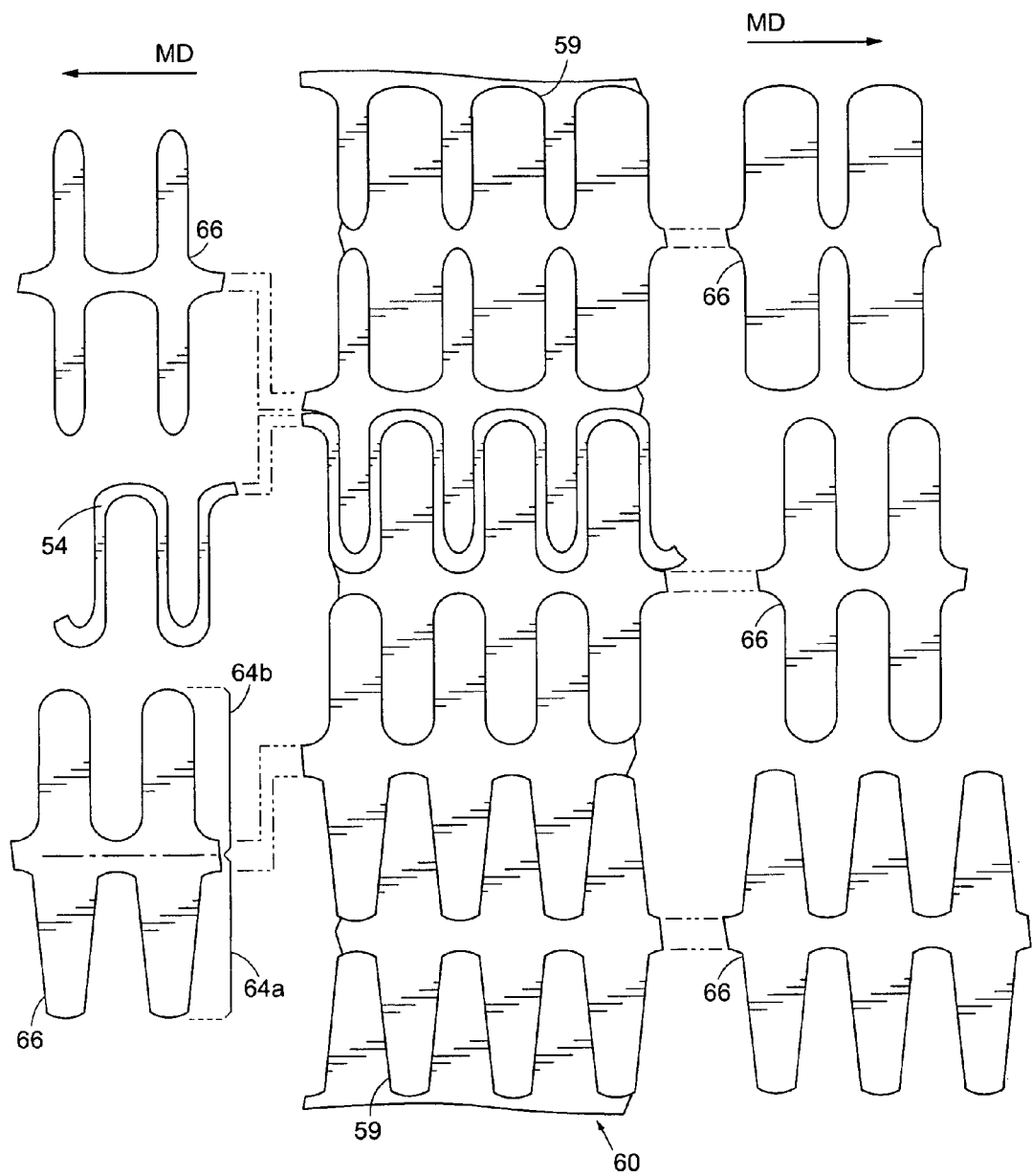
FIG. 22 is a fragmentary plan view illustrating a method of forming disparately configured strips of resilient members.

The interconnected resilient members illustrated thus far have been identical and symmetric. FIGS. 14a, 17a, and 22 illustrate examples, from many possible, of forming asymmetric or non-identical resilient members from resilient material 60. These embodiments further illustrate that complex resilient members can be formed without sacrificing resilient material to do so. FIG. 14a illustrates that the width of interconnected resilient members may be variable (along with the dimensions of interconnecting web 67) so as to produce non-identical resilient members from resilient material 60. Cut lines 59 of FIG. 14a form a pair of dissimilar nested strips 66 alternating in a repeating pattern across material 60. Said dissimilar strips 66 feature disparate resilient members adjacent each other, while the interconnected resilient members within each strip 66 are identical. Resilient material 60 includes base layer material 63 laminated thereto.

Figure 14C:
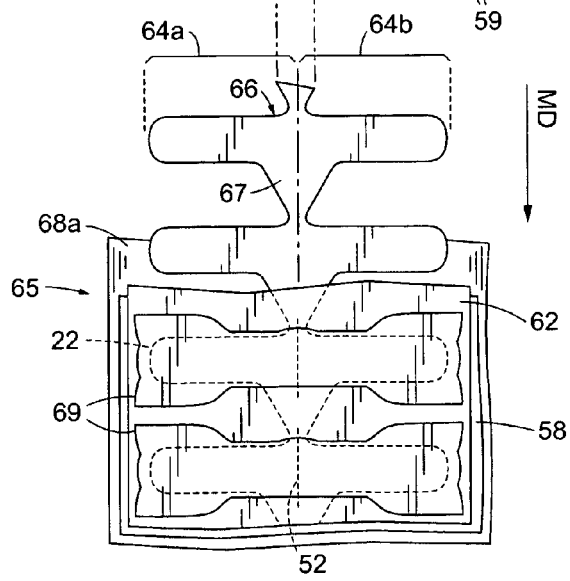

As discussed hereinbefore, cut lines 59 define each horizontal half of the interconnected resilient members of strip 66, and the width of a given resilient member corresponds to the spacing between resilient members nested adjacent thereto. The configuration of cut line 59 forming one long half of strip 66 in resilient material 60 also determines the configuration of one long half of the adjacent nested strip 66. In that sense the peripheral dimensions of the interconnected resilient members of one strip 66 are based on the peripheral dimensions of the interconnected resilient members 22 and webs 67 adjacent thereto. In this fashion, the material between two identical strips 66 within the material 60 matrix may be comparably formed as a non-identical, or disparate, strip 66. To further illustrate, brackets and dashed lines in FIGS. 14b and 14c show strip 66 divided by an imaginary centerline extending along its length (MD). Each long half is referenced 64a and 64b. The spacing between the resilient members of long half 64a in FIG. 14c corresponds to the resilient members' dimensions of long half 64b in FIG. 14b. Similarly, the configuration of web 67, which forms the spacing between interconnected resilient members of strip 66 in FIG. 14c, form end edges 23a and 23b of interconnected resilient members of strip 66 of FIG. 14b.

Figure 15:
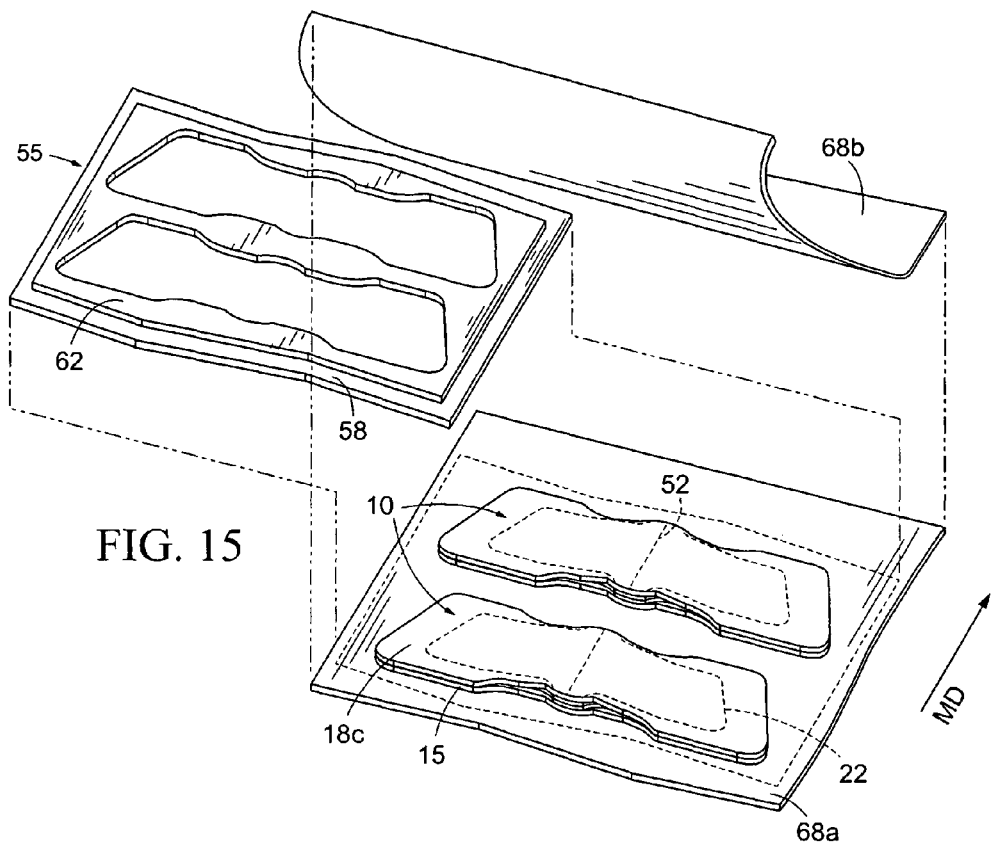
FIG. 15 is a fragmentary exploded perspective view illustrating the step of separating waste material from finished dilator units relative to the manufacturing method illustrated in FIGS. 14a and 14b.
Figure 16:
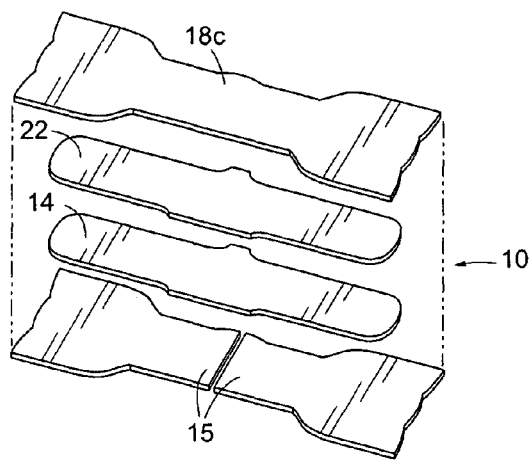
FIG. 16 is an exploded perspective view illustrating a finished dilator unit produced from the manufacturing method illustrated in FIGS. 14a and 14c.

To produce finished dilators 10 from fabrication matrix 65 of FIGS. 14b and 14c, alternating strips 66 are separated from the material 60 matrix and layered onto release paper liner 58 as described previously with respect to FIG. 5-8. Backscore 52 is then formed in liner 58, also as previously described, and cover material 62 is then layered on top of strip 66. The materials are layered onto packaging web 68a to complete the fabrication matrix 65. Die cut lines 69 then extend vertically to, but not through, packaging web 68a and waste matrix 55 is removed, leaving individual dilators 10 in a spaced apart relationship as more particularly illustrated in FIG. 15. FIG. 16 illustrates the vertically stacked layers of finished dilator units produced, in the same manner, from fabrication matrix 65 of FIG. 14c. From bottom to top its layers include release paper liner 15, base member 14, resilient member 22, and cover member 18c.

Cut lines 59 of FIG. 17a also form a pair of dissimilar nested strips 66 alternating in a repeating pattern across material 60. One strip 66 from said alternating pair has identical interconnected resilient members alternating in mirrored succession along the length (MD) thereof. The other of said pair features a resilient member with gradient upper and lower long edges followed by a resilient member with straight upper and lower edges, also alternating in succession. The spacing between the resilient members of long half 64a in FIG. 17b corresponds to the resilient members' dimensions of long half 64b in FIG. 17a. The former are incorporated into fabrication matrix 65 of FIGS. 17b and 17c, and the latter incorporated into fabrication matrix 65 of FIG. 17d.

FIGS. 17b and 17c illustrate strip 66 laminated onto base layer material 63 (material 60 does not include a base layer material laminated thereto). In lieu of a backscore, overlapping release paper liners 58 are placed underneath one or more base layer sheets 63. Cover layer material 62 exceeds at least the width of strip 66, and is laminated on top thereof to complete fabrication matrix 65. As shown in FIG. 17b, die cut lines 69 form individual dilator units around pairs of interconnected resilient members by severing every other interconnecting web 67 via cut line 70, instead of severing every one. Accordingly, two interconnected resilient members are combined into a single dilator unit. In FIG. 17c, die cut lines 69 form individual dilator units around each resilient member; the dilator units and resilient members being mirror images of each other, alternating in succession. In both FIGS. 17b and 17c, die cut lines 69 form substantial portions of the long edges of adjacent dilators 10 along common lines.

Figure 18:
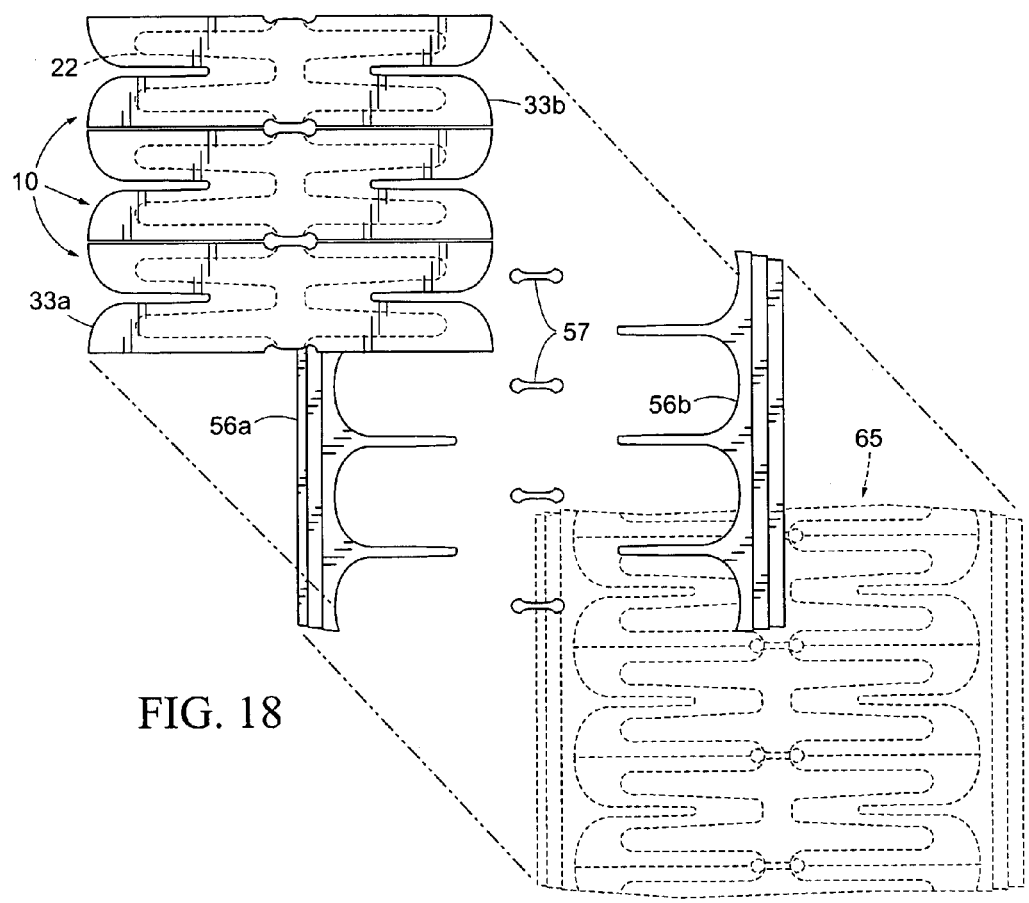
FIG. 18 is a fragmentary exploded plan view illustrating the step of separating finished dilator units from waste material relative to the manufacturing method of in FIGS. 17a and 17b.
Figure 19:
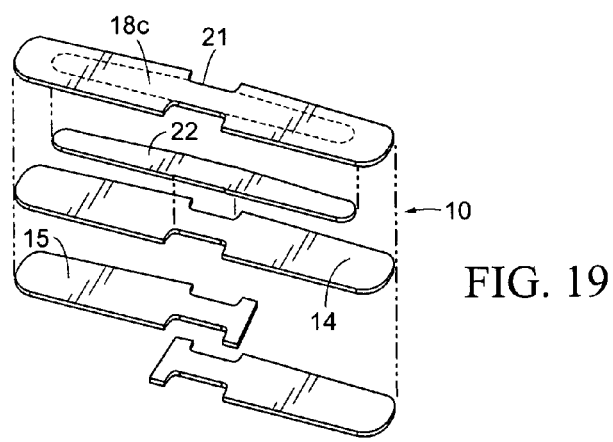
FIG. 19 is an exploded perspective view of the nasal dilator fabricated from the method illustrated in FIGS. 17a and 17c.

The fabrication matrixes 65 of FIGS. 17b and 17c yield dilator units using a similar method to that previously described with respect to FIGS. 11-13. FIG. 18 illustrates individual nasal dilator units produced from fabrication matrix 65 of FIG. 17b, separated from outside waste pieces 56a and 56b and center waste pieces 57. The resilient member of dilator 10 features upper and lower gradient, divergent, components extending horizontally outward from a common center. FIG. 19 illustrates the vertically stacked layers of finished dilator units, produced in the same manner, from fabrication matrix 65 of FIG. 17c. From bottom to top its layers include: overlapping release paper liner 15, base member 14, resilient member 22, and cover member 18c. Dilator 10 features a resilient member having a gradiently reduced width by virtue of its tapered upper long edges.

Figure 20:
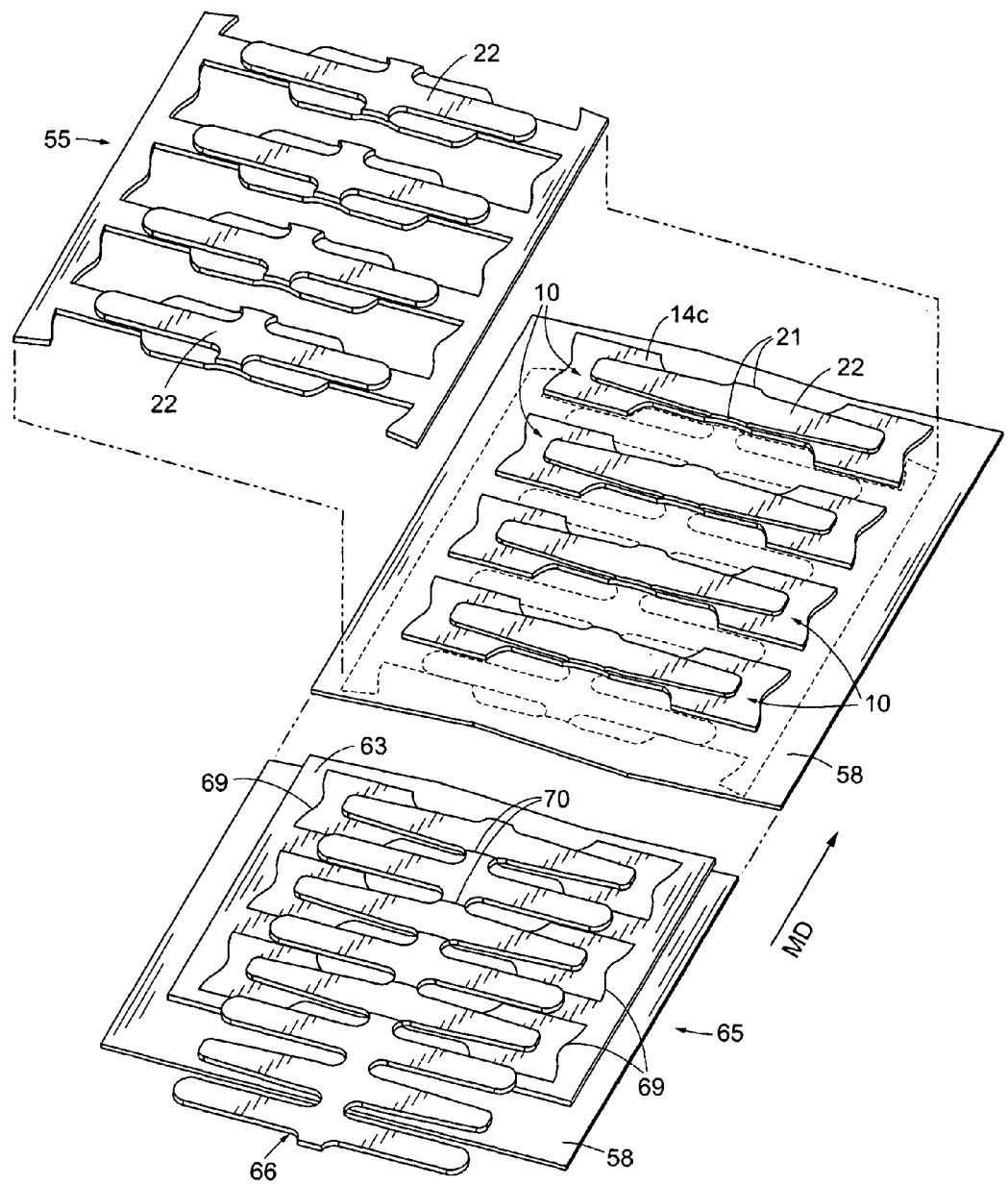

Returning briefly to FIG. 17a, the second strip 66 from said alternating pair of dissimilar nested strips 66, having the alternating non-identical interconnected resilient members, is incorporated into fabrication matrix 65 of FIG. 20. Die cut lines 69 form individual nasal dilator units around every other interconnected resilient member, creating a spaced apart relationship between finished dilator units. The process forms waste matrix 55 which is separated from fabrication matrix 65 leaving a plurality of identical individual dilators 10 upon release paper liner 58. Liner 58 may be die cut so as to separate dilators 10 individually or into groups and packaged for retail sale (in the same manner as previously shown in FIG. 9).

Waste matrix 55 includes irregular or discontinuous layers; portions thereof having been removed in the course of fabricating the finished dilator units of FIG. 20. Waste matrix 55 further includes the remaining identical, spaced apart, resilient members which were removed therewith. In this instance, waste matrix 55 is not discarded, but instead incorporated into another fabrication matrix 65, as more particularly illustrated in FIG. 21. For clarity, said re-incorporated waste matrix is renumbered supplemental matrix, 53.

Figure 21:
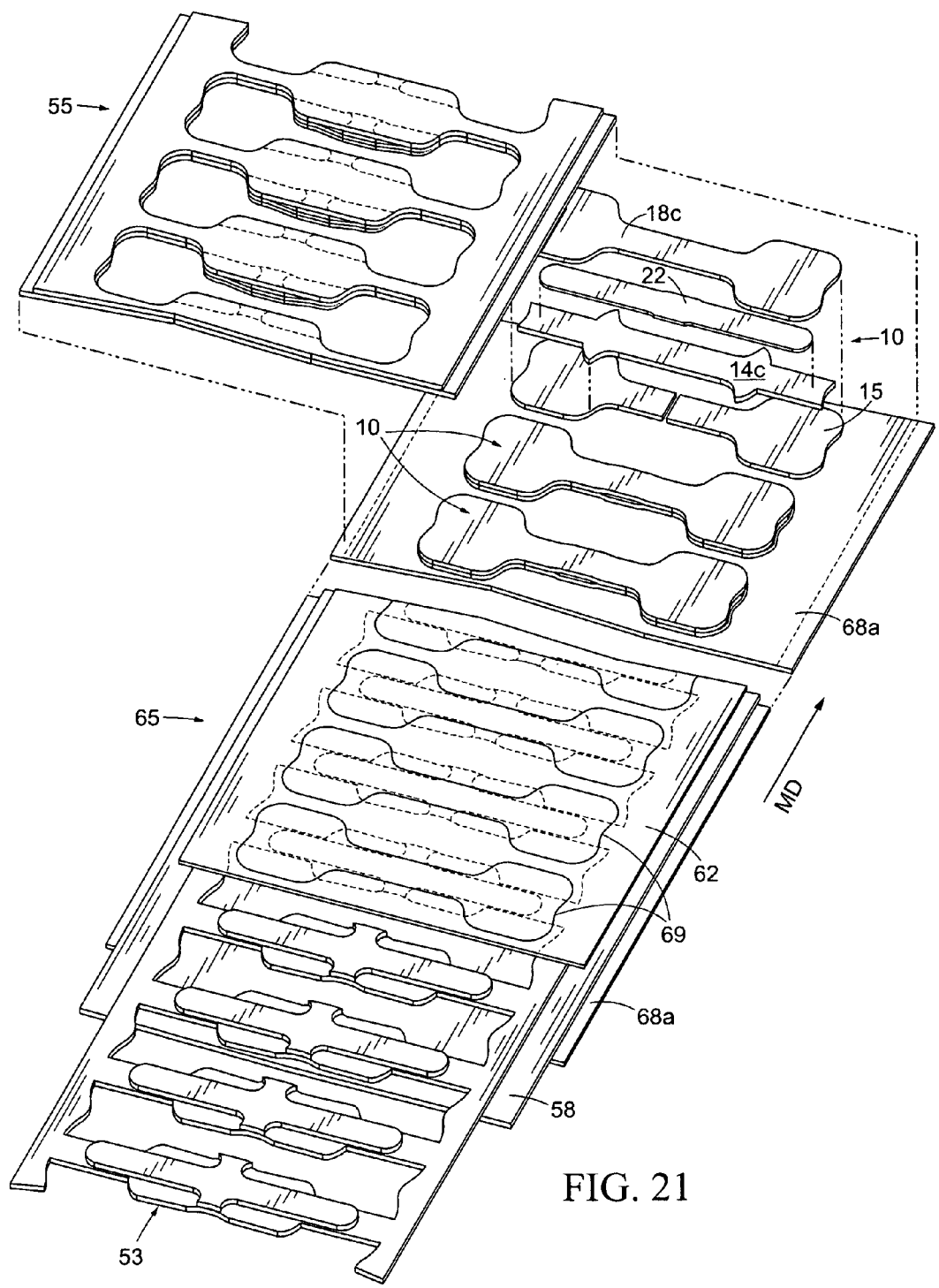
FIG. 21 is a fragmentary exploded perspective view illustrating the intermediate and final steps of a manufacturing method begun in FIG. 17a which utilizes waste material from the method illustrated in FIG. 20.

FIG. 21 illustrates supplemental matrix 53 being integrated into another fabrication matrix 65, and layered onto a new elongated paper liner 58, which may be backscored as discussed hereinbefore. Cover layer material 62 is layered on top thereof, and packaging web 68a again provides the foundation of fabrication matrix 65. Die cut lines 69 form individual nasal dilator units around each of said remaining spaced apart resilient members, cutting vertically through the laminate of fabrication matrix 65 to, but not through, packaging web 68a. Waste matrix 55 is separated from fabrication matrix 65, leaving individual dilators 10 in a spaced apart relationship on packaging web 68a. By virtue of re-using the waste matrix from the previous manufacturing operation, dilator 10 has an irregular or discontinuous base layer, as seen more particularly in the exploded perspective portion of FIG. 21. As discussed hereinbefore, an upper packaging web may be layered on top spaced apart dilators 10, forming a seal with packaging web 68a.

The alternating pattern of dissimilar nested strips 66 illustrated in the embodiments of FIGS. 14a and 17a is limited to a pair. The total number of repetitions of the pair, as well as the total number of individual strips 66 yielded, is limited by the dimensions of the material. To depart from this limitation of one pair of alternating dissimilar nested strips 66, FIG. 22 illustrates a method by which to incorporate additional disparate, strips 66 from resilient material 60. Cut lines 59 form a buffer section, 54, interposed between any two nested strips 66 and removed as waste when separating them from material 60. Buffer section 54 may be any necessary width, but is preferably as narrow as practicable. In the alternative, one long half of at least one strip 66 may be configured into one half of a new and different pattern. As further illustrated in FIG. 22, cut line 59 may be used as a new pattern where it forms long half 64a, by repeating in mirrored succession to form long halves 64a and 64b of successive nested strips 66.

It will be obvious to the skilled man that the placement and configuration of cut lines 59 and 69 in the manufacturing methods taught herein are variable while remaining within the scope of the present invention. In particular, cut lines 59 form interconnecting web 67 along the upper and lower long edges of resilient member 22, substantially midway between its end edges 23a and 23b. However, said position may correspond to intermediate region 36 of truss 30, and thus further contribute to the disparity between adjacent nested strips 66.

As illustrated and described in examples of the preferred embodiments, the present invention provides nasal dilator devices and methods of manufacture that utilize techniques to create efficiencies which use less material without increasing fabrication costs, that configure device elements to be fabricated along common lines or edges that define their peripheral dimensions and simultaneously create a spaced apart relationship therebetween without sacrificing usable material to do so; that provide, as a result, a wide range of diverse and disparate nasal dilator devices that may be competitively manufactured, that are simple and easy to use, and that effectively dilate external tissue.

I claim:

1. A method of fabricating a plurality of resilient members configured for incorporation into a laminated fabrication matrix from which to produce a plurality of tissue dilators, comprising:
   a) cutting through an elongated sheet of thermoplastic material along at least three prescribed lines so as to form a plurality of successive individual resilient members interconnected by webs, the webs integrating said individual resilient members into an elongated strip, the prescribed lines spaced apart across the thermoplastic material such that said cutting through forms a plurality of said elongated strips nested adjacent each other in a repeating pattern, the cutting through along each two adjacent spaced apart prescribed lines thus forming a single elongated strip; and c) separating at least one elongated strip from the thermoplastic material, wherein
the thermoplastic material has substantial in-plane rigidity and out-of-plane flexibility, the material further having a thickness of from about 0.005" to about 0.015".

2. The method of claim 1 in which a long half of said elongated strip corresponds to a long half of the elongated strip nested adjacent thereto.

3. The method of claim 1 wherein a long edge of the interconnecting web corresponds to an end edge of the interconnected resilient member nested adjacent thereto.

4. The method of claim 1 wherein said elongated sheet, said prescribed lines, and said elongated strip are oriented parallel to a machine direction, the interconnected resilient members being thus oriented substantially perpendicular to said machine direction.

5. The method of claim 1 wherein the prescribed lines extend substantially from a long edge of the thermoplastic material to an opposite long edge thereof, so as to form the elongated strip oriented perpendicular to a machine direction, the interconnected resilient members being thus oriented substantially parallel to said machine direction.

6. The method of claim 1 wherein said cutting step comprises cutting along at least four prescribed lines, two of said at least four prescribed lines being generally parallel to each other and forming an elongated buffer section interposed between two adjacent nested elongated strips.

7. A method of manufacturing a tissue dilator comprising the steps of:
a) forming a plurality of elongated strips by cutting through an elongated sheet of thermoplastic material along a plurality of prescribed lines, said prescribed lines spaced apart across the thermoplastic material in a repeating pattern, the cutting operations forming the elongated strips nested adjacent each other, each elongated strip comprising a plurality of spaced apart resilient members interconnected by webs, the elongated sheet of thermoplastic material having substantial in-plane rigidity and out-of-plane flexibility, and further having a thickness of from about 0.005" to about 0.015";
b) forming a fabrication matrix by separating one or more of said elongated strips and combining the one or more separated strips with at least one elongated sheet of flexible material; and
c) cutting vertically through the fabrication matrix along prescribed lines extending around a predetermined number of the interconnected resilient members, said cutting vertically further selectively severing a prescribed number of the interconnecting webs so as to form a plurality of finished dilators, each finished dilator having a material separation along upper and lower long edges of an intermediate region thereof, a portion of a long edge of the resilient member being visible at said material separation.

8. The method of claim 7 wherein the fabrication matrix further comprises upper and lower packaging webs; and
a) wherein said cutting vertically through the fabrication matrix forms a spaced apart relationship between finished dilators sufficient so as to allow the upper and lower packaging webs to form an adequate seal between finished tissue dilators.

9. The method of claim 7 in which said cutting vertically through the fabrication matrix extends to, but not through, a release paper liner; and
a) removing waste material so as to leave finished dilators in a spaced apart relationship upon the liner.

10. The method of claim 7 wherein said cutting vertically forms a long edge of two adjacent dilators along a portion of said prescribed lines.

11. The method of claim 7 wherein said cutting vertically forms a waste matrix comprising a continuous portion of said fabrication matrix including a plurality of severed resilient members as part thereof, said waste matrix to be processed further to produce additional dilators.

12. The method of claim 7 wherein every other interconnecting web is severed so as to combine two successive resilient members and the interconnecting web therebetween into a single resilient member of a finished dilator.

13. The method of claim 1 and further including a process for forming said laminated fabrication matrix and producing said plurality of tissue dilators, comprising the steps of:
a) combining the at least one elongated strip separated from the thermoplastic material with at least one of an elongated sheet of base layer or cover layer material to produce the laminated fabrication matrix;
b) cutting vertically through the laminated fabrication matrix along peripheral lines extending around a predetermined number of the interconnected resilient members, the peripheral lines defining peripheral edges of finished tissue dilators, said cutting vertically further selectively severing predetermined interconnecting webs; and
c) removing waste material extending outboard of said peripheral edges of finished tissue dilators so as to separate the waste material from the fabrication matrix, a portion of a long edge of the resilient member corresponding to a cross sectional portion of an interconnecting web thus being exposed along a portion of a long edge of each finished tissue dilator where said predetermined interconnecting webs are severed from said at least one elongated strip.

14. The method of claim 1 wherein each prescribed line defines a substantial portion of a long half of two adjacent nested elongated strips.

15. The method of claim 1 wherein a length of the interconnecting webs defines a distance between the interconnected resilient members.

16. The method of claim 1 wherein the interconnecting webs are positioned approximately midway along resilient member upper and lower long edges, said long edges extending roughly perpendicular to a longitudinal direction of the elongated strip.

17. The method of claim 16 wherein a portion of the interconnecting web forms a portion the interconnected resilient member contiguous thereto and further defines a portion of the interconnected resilient member adjacent thereto.

18. The method of claim 1 wherein the interconnected resilient members within a successive group are substantially identical, or a predetermined number of resilient members within said group are substantially identical.

19. The method of claim 1 wherein the interconnected resilient members of an elongated strip are non-identical to the interconnected resilient members of an elongated strip adjacent thereto.

20. The method of claim 7 wherein said selectively severing the interconnecting webs forms identical and non-identical resilient members.

21. The method of claim 13 wherein said selectively severing a prescribed number of the interconnecting webs combines successive resilient members and interconnecting web(s) therebetween into a single element resilient member having at least one divergent spring finger component extending into a first end region of said finished tissue dilator and at least two divergent spring finger components extending into a second end region of said finished tissue dilator.

22. The method of claim 13 wherein:
said peripheral lines and said selectively severing predetermined interconnecting webs correspond to a first plurality of said predetermined resilient members, the first plurality corresponding to said finished tissue dilators, the laminated fabrication matrix being a first fabrication matrix;
said waste material extends outboard of said peripheral edges of finished tissue dilators, the waste material comprising a continuous matrix including a second plurality of predetermined resilient members;
and further including;
a) combining the continuous matrix with at least one of an elongated sheet of base layer or cover layer material to produce a second laminated fabrication matrix; and
b) cutting vertically through the second laminated fabrication matrix along peripheral lines extending around at least a predetermined number of said second plurality of resilient members, the peripheral lines defining peripheral edges of finished tissue dilators.

23. The method of claim 22 wherein at least some of said peripheral edges are defined such that the resilient member is wholly contained within said peripheral edges.

24. The method of claim 22 wherein at least some of the second predetermined number of resilient members are selectively non-severed such that at least two successive resilient members and the interconnecting web or webs therebetween are combined into a single resilient member, the single resilient member having at least two divergent spring finger components extending into a first end region of said finished tissue dilator and at least two divergent spring finger components extending into a second end region of said finished tissue dilator.

25. A method of fabricating a plurality of nasal dilators, comprising:
slitting a uniform strip of resilient member material into a plurality of nested sub-strips, each nested sub-strip comprising a plurality of oblong resilient-member shapes joined to at least one adjacent oblong resilient-member shape by an interconnecting resilient member material web located at about a midpoint of a long side of the resilient-member shape;
separating a first nested sub-strip from other sub-strips of the plurality of nested sub-strips;
laminating the first nested sub-strip to one of a base layer or a cover layer to form a laminated strip comprising a plurality of interconnected nasal dilator precursors; and
cutting the laminated strip of nasal dilator precursors along an outer boundary to form a plurality of separate nasal dilators, said outer boundary crossing the interconnecting resilient member material web and severing one nasal dilator from an adjacent nasal dilator.

26. The method of claim 25, further comprising:
separating a second nested sub-strip from the other sub-strips of the plurality of nested sub-strips; and
repeating the laminating and cutting operations on the second sub-strip to produce a second plurality of separate nasal dilators.

\* \* \* \* \*